(12) United States Patent
Kim et al.

(10) Patent No.: US 9,412,957 B2
(45) Date of Patent: Aug. 9, 2016

(54) CASCADE-TYPE COMPOUND AND ORGANIC LIGHT-EMITTING DEVICE INCLUDING THE SAME

(71) Applicants: SAMSUNG DISPLAY CO., LTD., Yongin, Gyeonggi-do (KR); INDUSTRY-ACADEMIC COOPERATION FOUNDATION GYEONGSANG NATIONAL UNIVERSITY, Gyeongnam (KR)

(72) Inventors: Se-Hun Kim, Yongin (KR); Mie-Hwa Park, Yongin (KR); Sam-Il Koh, Yongin (KR); Mi-Kyung Kim, Yongin (KR); Kwan-Hee Lee, Yongin (KR); Yun-Hi Kim, Yongin (KR)

(73) Assignees: Samsung Display Co., Ltd., Samsung-ro, Giheung-Gu, Yongin-si, Gyeonggi-Do (KR); INDUSTRY-ACADEMIC COOPERATION FOUNDATION GYEONGSANG NATIONAL UNIVERSITY, Jinjun, Gyeongnam (KR)

( * ) Notice: Subject to any disclaimer, the term of this patent is extended or adjusted under 35 U.S.C. 154(b) by 668 days.

(21) Appl. No.: 13/745,604

(22) Filed: Jan. 18, 2013

(65) Prior Publication Data

US 2014/0054558 A1 Feb. 27, 2014

(30) Foreign Application Priority Data

Aug. 22, 2012 (KR) .................. 10-2012-0091991

(51) Int. Cl.
  *H01L 51/00* (2006.01)
  *C07F 7/08* (2006.01)
  *H01L 51/50* (2006.01)

(52) U.S. Cl.
  CPC ............ *H01L 51/0094* (2013.01); *C07F 7/082* (2013.01); *C07F 7/0809* (2013.01);
  (Continued)

(58) Field of Classification Search
  None
  See application file for complete search history.

(56) References Cited

U.S. PATENT DOCUMENTS

| 5,635,308 A | 6/1997 | Inoue et al. |
| 7,839,074 B2 | 11/2010 | Ikeda et al. |
| 2006/0008674 A1 | 1/2006 | Yu et al. |
| 2006/0043858 A1 | 3/2006 | Ikeda et al. |

FOREIGN PATENT DOCUMENTS

| JP | 03-200289 A | 9/1991 |
| JP | 07-138561 A | 5/1995 |

(Continued)

OTHER PUBLICATIONS

C.W. Tang et al., Organic Electroluminescent Diodes, American Institute of Physics, Sep. 21, 1987, vol. 51, No. 12, pp. 913-915.

(Continued)

*Primary Examiner* — J. L. Yang
(74) *Attorney, Agent, or Firm* — Robert E. Bushnell, Esq.

(57) ABSTRACT

A cascade-type compound and an organic light-emitting device (OLED) including the same are provided. The cascade-type compound can be generically represented as Formula 1 below:

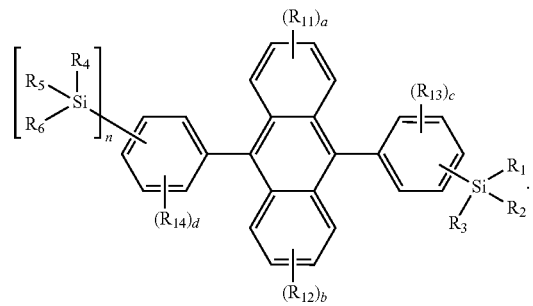

<Formula 1>

15 Claims, 1 Drawing Sheet

(52) U.S. Cl.
CPC .......... *C07F 7/0812* (2013.01); *H01L 51/0058* (2013.01); *H01L 51/0052* (2013.01); *H01L 51/0054* (2013.01); *H01L 51/5012* (2013.01); *H01L 2251/308* (2013.01)

(56) References Cited

FOREIGN PATENT DOCUMENTS

| | | |
|---|---|---|
| JP | 08-012600 A | 1/1996 |
| JP | 08-239655 A | 9/1996 |
| JP | 2006-028175 A | 2/2006 |
| JP | 2009-292806 A | 12/2009 |
| KR | 10-0924462 B1 | 10/2009 |
| KR | 10-0946476 B1 | 3/2010 |
| KR | 10-2011-0123701 A | 11/2011 |

OTHER PUBLICATIONS

Japan Chemical Substance Dictionary Service (http://nikkajiweb.jst.go.jp/nikkaji_web/pages/top.jsp?CONTENT=syosai&SN=J2.307.808B).

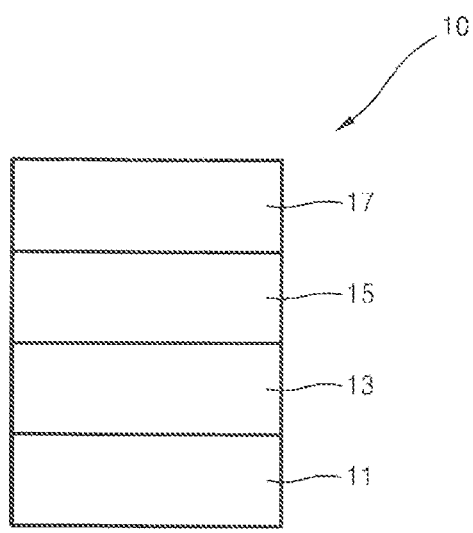

CASCADE-TYPE COMPOUND AND ORGANIC LIGHT-EMITTING DEVICE INCLUDING THE SAME

CLAIM OF PRIORITY

This application makes reference to, incorporates the same herein, and claims all benefits accruing under 35 U.S.C. §119 from and application for CASCADE-TYPE COMPOUND AND ORGANIC LIGHT-EMITTING DEVICE INCLUDING THE SAME earlier filed in the Korean Intellectual Property Office on 22 Aug. 2012 and there duly assigned Serial No. 10-2012-0091991.

BACKGROUND OF THE INVENTION

1. Field of the Invention

The present invention relates to a compound for organic light-emitting devices, and an organic light-emitting device including the compound.

2. Description of the Related Art

Organic light-emitting devices (OLEDs), which are self-emitting devices, have advantages such as wide viewing angles, excellent contrast, quick response, high brightness, excellent driving voltage characteristics, and the ability to provide multicolored images.

A typical OLED has a structure including a substrate, an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY OF THE INVENTION

The present invention provides a cascade-type compound having a novel structure and an organic light-emitting device including the cascade-type compound.

According to an aspect of the present invention, there is provided a cascade-type compound represented by Formula 1 below:

<Formula 1>

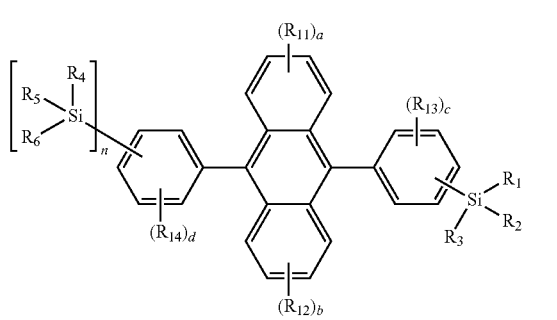

wherein, in Formula 1, n is 0 or 1;

$R_1$ and $R_4$ are each independently a substituted or unsubstituted $C_1$-$C_{60}$ alkyl group, or a 3- to 10-membered substituted or unsubstituted non-condensed ring group;

$R_2$ and $R_5$ are each independently a substituted or unsubstituted $C_1$-$C_{60}$ alkyl group, a 3- to 10-membered substituted or unsubstituted non-condensed ring group, or a substituted or unsubstituted condensed ring group in which at least two rings are fused with each other;

$R_3$ is a substituted or unsubstituted condensed ring group in which at least two rings are fused to each other;

$R_6$ is a 3- to 10-membered substituted or unsubstituted non-condensed ring group; or a substituted or unsubstituted condensed ring group in which at least two rings are fused to each other;

$R_{11}$ to $R_{14}$ are each independently a hydrogen atom, a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($Q_1$)($Q_2$), or —Si($Q_3$)($Q_4$)($Q_5$), wherein $Q_1$ to $Q_5$ are each independently a hydrogen atom, a $C_1$-$C_{10}$ alkyl group, a $C_6$-$C_{20}$ aryl group, or a $C_2$-$C_{20}$ heteroaryl group;

a, b and c are each independently an integer from 1 to 4; and d is an integer from 1 to 5, provided that a compound where n is 1 and all of $R_3$ and $R_6$ are unsubstituted pyenyl groups is excluded.

According to another aspect of the present invention, there is provided an organic light-emitting device including a first electrode, a second electrode disposed opposite to the first electrode, and an organic layer disposed between the first electrode and the second electrode, the organic layer including at least one of the cascade-type compounds of Formula 1 above.

BRIEF DESCRIPTION OF THE DRAWING

The above and other features and advantages of the present invention will become more apparent by describing in detail exemplary embodiments thereof with reference to the attached drawing in which:

FIG. 1 schematically illustrates the structure of an organic light-emitting device according to an embodiment of the present invention.

DETAILED DESCRIPTION OF THE INVENTION

As used herein, the term "and/or" includes any and all combinations of one or more of the associated listed items. Expressions such as "at least one of", when preceding a list of elements, modify the entire list of elements and do not modify the individual elements of the list.

According to an aspect of the present invention, there is provided a cascade-type compound represented by Formula 1.

<Formula 1>

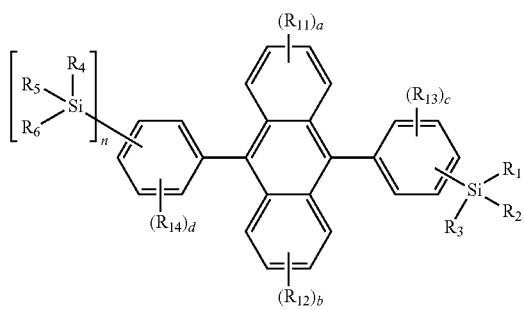

In Formula 1 above, n may be 0 or 1. If n is 0, Formula 1 does not include the substituent —Si(R$_4$)(R$_5$)(R$_6$).

The compound of Formula 1 may be represented by any one of the following Formulae 1A to 1F, but is not limited thereto.

<Formula 1A>

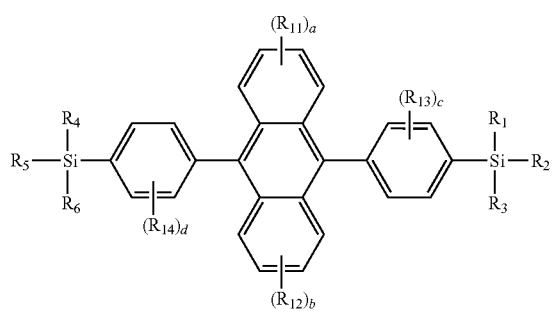

<Formula 1B>

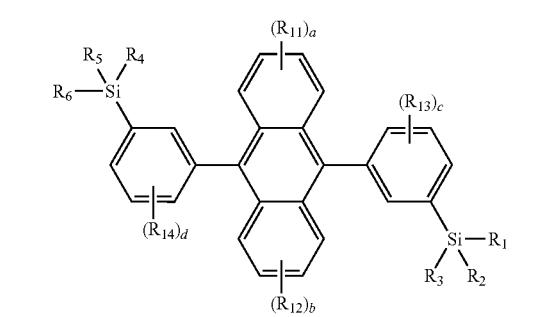

<Formula 1C>

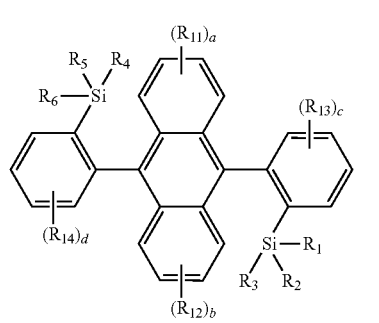

<Formula 1D>

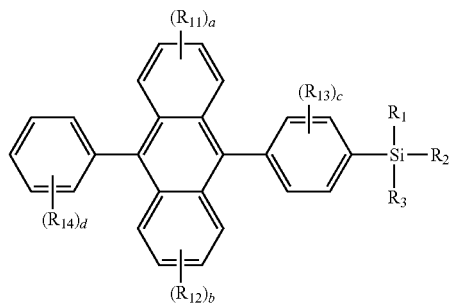

<Formula 1E>

<Formula 1F>

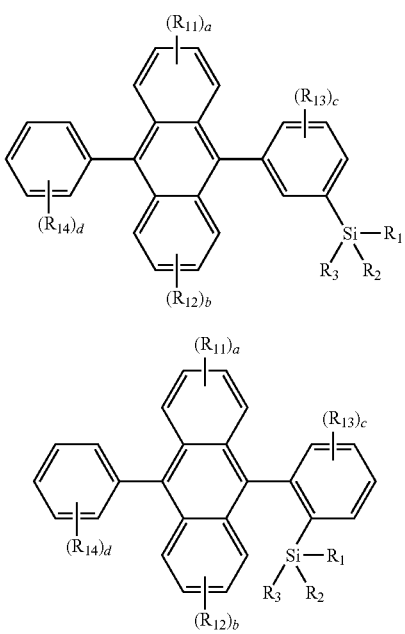

For example, the cascade-type compound may be represented by Formula 1A or 1D but is not limited thereto.

In Formula 1, $R_1$ and $R_4$ may be each independently a substituted or unsubstituted $C_1$-$C_{60}$ alkyl group, or a 3- to 10-membered substituted or unsubstituted non-condensed ring group; $R_2$ and $R_5$ may be each independently a substituted or unsubstituted $C_1$-$C_{60}$ alkyl group, a 3- to 10-membered substituted or unsubstituted non-condensed ring group, or a substituted or unsubstituted condensed ring group in which at least two rings are fused with each other; $R_3$ may be substituted or unsubstituted condensed ring group in which at least two rings are fused to each other; and $R_6$ is a 3- to 10-membered substituted or unsubstituted non-condensed ring group or a substituted or unsubstituted condensed ring group in which at least two rings are fused to each other, In Formula 1, $R_1$ and $R_4$ are not "substituted or unsubstituted condensed ring groups in which at least two rings are fused to each other", and $R_3$ or $R_3$ and $R_6$ are "substituted or unsubstituted condensed ring groups in which at least two rings are fused to each other". Accordingly, there is no incidence when all of $R_1$ to $R_6$ in Formula 1 are the same.

As used herein, the phrase "the 3- to 10-membered substituted or unsubstituted non-condensed ring group" refers to a 3- to 10-membered cyclic group with one ring unable to form a condensed ring. Ring-member atoms of "the 3- to 10-membered substituted or unsubstituted non-condensed ring group" may be selected from among C, N, O, P, S, and Si. This will be understood with reference to Formulae 2A to 2T described below.

As used herein, the phrase "condensed ring group with condensed at least two substituted or unsubstituted rings" refers to a group with at least two rings that are fused to each other. The "condensed ring group with condensed at least two substituted or unsubstituted rings" may be an aromatic or non-aromatic group, and may include 3 to 60 ring-member atoms, wherein these ring-member atoms may be selected from among C, N, O, P, S, and Si. The "condensed ring group with condensed at least two substituted or unsubstituted rings" will be understood with reference to, for example. Formulae 3A to 3R and Formulae 4A to 4J described below.

In some embodiments, in Formula 1 above, $R_1$ and $R_4$ may be each independently a substituted or unsubstituted $C_1$-$C_{20}$ alkyl group, a substituted or unsubstituted cyclopropyl group, a substituted or unsubstituted cyclobutyl group, a substituted or unsubstituted cyclopentyl group, a substituted or unsubstituted cyclohexyl group, a substituted or unsubstituted cycloheptyl group, a substituted or unsubstituted cyclooctyl group, a substituted or unsubstituted cyclopentenyl group, a substituted or unsubstituted cyclopentadienyl group, a substituted or unsubstituted cyclohexcenyl group, a substituted or unsubstituted cyclohexadienyl group, a substituted or unsubstituted cycloheptadienyl group, a substituted or unsubstituted thiophenyl group, a substituted or unsubstituted furanyl group, a substituted or unsubstituted pyrrolyl group, a substituted or unsubstituted imidazolyl group, a substituted or unsubstituted pyrazolyl group, a substituted or unsubstituted isothiazolyl group, a substituted or unsubstituted isoxazolyl group, a substituted or unsubstituted thiazolyl group, a substituted or unsubstituted oxazolyl group, a substituted or unsubstituted oxadiazolyl group, a substituted or unsubstituted thiadiazolyl group, a substituted or unsubstituted triazolyl group, a substituted or unsubstituted phenyl group, a substituted or unsubstituted pyridinyl group, a substituted or unsubstituted pyrazinyl group, a substituted or unsubstituted pyrimidinyl group, a substituted or unsubstituted pyridazinyl group, or a substituted or unsubstituted triazinyl group;

$R_2$ and $R_5$ may be each independently a substituted or unsubstituted $C_1$-$C_{20}$ alkyl group, a substituted or unsubstituted cyclopropyl group, a substituted or unsubstituted cyclobutyl group, a substituted or unsubstituted cyclopentyl group, a substituted or unsubstituted cyclohexyl group, a substituted or unsubstituted cycloheptyl group, a substituted or unsubstituted cyclooctyl group, a substituted or unsubstituted cyclopentenyl group, a substituted or unsubstituted cyclopentadienyl group, a substituted or unsubstituted cyclohexcenyl group, a substituted or unsubstituted cyclohexadienyl group, a substituted or unsubstituted cycloheptadienyl group, a substituted or unsubstituted thiophenyl group, a substituted or unsubstituted furanyl group, a substituted or unsubstituted pyrrolyl group, a substituted or unsubstituted imidazolyl group, a substituted or unsubstituted pyrazolyl group, a substituted or unsubstituted isothiazolyl group, a substituted or unsubstituted isoxazolyl group, a substituted or unsubstituted thiazolyl group, a substituted or unsubstituted oxazolyl group, a substituted or unsubstituted oxadiazoyl group, a substituted or unsubstituted thiadiazolyl group, a substituted or unsubstituted triazolyl group, a substituted or unsubstituted phenyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted triazinyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted biphenylenyl group, a substituted or unsubstituted indacenyl group, a substituted or unsubstituted acenaphthylenyl group, a substituted or unsubstituted fluorenyl group, a substituted or unsubstituted spiro-fluorenyl group, a substituted or unsubstituted carbazolyl group, a substituted or unsubstituted anthryl group, a substituted or unsubstituted phenalenyl group, a substituted or unsubstituted phenanthrenyl group, a substituted or unsubstituted chrysenyl group, a substituted or unsubstituted triphenylenyl group, a substituted or unsubstituted pyrenyl group, a substituted or unsubstituted perylenyl group, a substituted or unsubstituted fluoranthenyl group, a substituted or unsubstituted naphthacenyl group, a substituted or unsubstituted picenyl group, a substituted or unsubstituted pentaphenyl group, a substituted or unsubstituted hexacenyl group, a substituted or unsubstituted dibenzofuranyl group, a substituted or unsubstituted dibenzothiophenyl group, a substituted or unsubstituted phenothiazinyl group, a substituted or unsubstituted phenoxazinyl group, a substituted or unsubstituted dihydrophenazinyl group, a substituted or unsubstituted phenoxathiinyl group, and a substituted or unsubstituted phenanthridinyl group;

$R_3$ may be a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted biphenylenyl group, a substituted or unsubstituted indacenyl group, a substituted or unsubstituted acenaphthylenyl group, a substituted or unsubstituted fluorenyl group, a substituted or unsubstituted spiro-fluorenyl group, a substituted or unsubstituted carbazolyl group, a substituted or unsubstituted anthryl group, a substituted or unsubstituted phenalenyl group, a substituted or unsubstituted phenanthrenyl group, a substituted or unsubstituted chrysenyl group, a substituted or unsubstituted triphenylenyl group, a substituted or unsubstituted pyrenyl group, a substituted or unsubstituted perylenyl group, a substituted or unsubstituted fluoranthenyl group, a substituted or unsubstituted naphthacenyl group, a substituted or unsubstituted picenyl group, a substituted or unsubstituted pentaphenyl group, a substituted or unsubstituted hexacenyl group, a substituted or unsubstituted dibenzofuranyl group, a substituted or unsubstituted dibenzothiophenyl group, a substituted or unsubstituted phenothiazinyl group, a substituted or unsubstituted phenoxazinyl group, a substituted or unsubstituted dihydrophenazinyl group, a substituted or unsubstituted phenoxathiinyl group, or a substituted or unsubstituted phenanthridinyl group; and $R_6$ may be a substituted or unsubstituted cyclopropyl group, a substituted or unsubstituted cyclobutyl group, a substituted or unsubstituted cyclopentyl group, a substituted or it unsubstituted cyclohexyl group, a substituted or unsubstituted cycloheptyl group, a substituted or unsubstituted cyclooctyl group, a substituted or unsubstituted cyclopentenyl group, a substituted or unsubstituted cyclopentadienyl group, a substituted or unsubstituted cyclohexcenyl group, a substituted or unsubstituted cyclohexadienyl group, a substituted or unsubstituted cycloheptadienyl group, a substituted or unsubstituted thiophenyl group, a substituted or unsubstituted furanyl group, a substituted or unsubstituted pyrrolyl group, a substituted or unsubstituted imidazolyl group, a substituted or unsubstituted pyrazolyl group, a substituted or unsubstituted isothiazolyl group, a substituted or unsubstituted isoxazolyl group, a substituted or unsubstituted thiazolyl group, a substituted or unsubstituted oxazolyl group, a substituted or unsubstituted oxadiazolyl group, a substituted, or unsubstituted thiadiazolyl group, a substituted or unsubstituted triazolyl group, a substituted, or unsubstituted phenyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted triazinyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted biphenylenyl group, a substituted or unsubstituted indacenyl group, a substituted or unsubstituted acenaphthylenyl group, a substituted or unsubstituted fluorenyl group, a substituted or unsubstituted spiro-fluorenyl group, a substituted or unsubstituted carbazolyl group, a substituted or unsubstituted anthryl group, a substituted or unsubstituted phenalenyl group, a substituted or unsubstituted phenanthrenyl group, a substituted or unsubstituted chrysenyl group, a substituted or unsubstituted triphenylenyl group, a substituted or unsubstituted pyrenyl group, a substituted or unsubstituted perylenyl group, a substituted or unsubstituted fluoranthenyl group, a substituted or unsubstituted naphthacenyl group, a substituted or unsubstituted picenyl group, a substituted or unsubstituted pentaphenyl group, a substituted or unsubstituted hexacenyl group, a substituted or unsubstituted dibenzofuranyl group, a substituted or unsubstituted dibenzothiophenyl group, a substituted or unsubstituted phenothiazinyl group, a substituted or unsubstituted phenoxazinyl group, a substituted or unsubstituted dihydrophenazinyl group, a substituted or unsubstituted phenoxathiinyl group, or a substituted or unsubstituted phenanthridinyl group.

In some other embodiments, in Formula 1 above, $R_1$ to $R_4$ may be each independently one of a $C_1$-$C_{20}$ alkyl group, a cyclopropyl group, a cyclobutyl group, a cyclopentyl group, a cyclohexyl group, a cycloheptyl group, a cyclooctyl group, a cyclopentenyl group, a cyclopentadienyl group, a cyclohexcenyl group, a cyclohexadienyl group, a cycloheptadienyl group, a thiophenyl group, a furanyl group, a pyrrolyl group, an imidazolyl group, a pyrazolyl group, an isothiazolyl group, an isoxazolyl group, a thiazolyl group, an oxazolyl group, an oxadiazolyl group, a thiadiazolyl group, a triazolyl group, a phenyl group, a pyridinyl group, a pyrazinyl group, a pyrimidinyl group, a pyridazinyl group, and a triazinyl group; and a $C_1$-$C_{20}$ alkyl group, a cyclopropyl group, a cyclobutyl group, a cyclopentyl group, a cyclohexyl group, a cycloheptyl group, a cyclooctyl group, a cyclopentenyl group, a cyclopentadienyl group, a cyclohexcenyl group, a cyclohexadienyl group, a cycloheptadienyl group, a thiophenyl group, a furanyl group, a pyrrolyl group, an imidazolyl group, a pyrazolyl group, an isothiazolyl group, an isoxazolyl group, a thiazolyl group, an oxazolyl group, an oxadiazolyl group, a thiadiazolyl group, a triazolyl group, a phenyl group, a pyridinyl group, a pyrazinyl group, a pyrimidinyl group, a pyridazinyl group, and a triazinyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —N($Q_{11}$)($Q_{12}$), wherein $Q_{11}$ and $Q_{12}$ are each independently a hydrogen atom, a $C_1$-$C_{10}$ alkyl group, a $C_6$-$C_{20}$ aryl group or a $C_2$-$C_{20}$ heteroaryl group;

$R_2$ and $R_5$ may be each independently one of a $C_1$-$C_{20}$ alkyl group, a cyclopropyl group, a cyclobutyl group, a cyclopentyl group, a cyclohexyl group, a cycloheptyl group, a cyclooctyl group, a cyclopentenyl group, a cyclopentadienyl group, a cyclohexenyl group, a cyclohexadienyl group, a cycloheptadienyl group, a thiophenyl group, a furanyl group, a pyrrolyl group, an imidazolyl group, a pyrazolyl group, an isothiazolyl group, an isoxazolyl group, a thiazolyl group, an oxazolyl group, an oxadiazolyl group, a thiadiazolyl group, a triazolyl group, a phenyl group, a pyridinyl group, a pyrazinyl group, a pyrimidinyl group, a pyridazinyl group, a triazinyl group, a pentalenyl group, an indenyl group, a naphthyl group, an azulenyl group, a heptalenyl group, a biphenylenyl group, an indacenyl group, an acenaphthylenyl group, a fluorenyl group, a spiro-fluorenyl group, a carbazolyl group, an anthryl group, a phenalenyl group, a phenanthrenyl group, a perylenyl group, a fluoranthenyl group, a naphthacenyl group, a picenyl group, a pentaphenyl group, a hexacenyl group, a dibenzofuranyl group, a dibenzothiophenyl group, a phenothiazinyl group, a phenoxazinyl group, a dihydrophenazinyl group, a phenoxathiinyl group, and a phenanthridinyl group; and a $C_1$-$C_{20}$ alkyl group, a cyclopropyl group, a cyclobutyl group, a cyclopentyl group, a cyclohexyl group, a cycloheptyl group, a cyclooctyl group, a cyclopentenyl group, a cyclopentadienyl group, a cyclohexcenyl group, a cyclohexadienyl group, a cycloheptadienyl group, a thiophenyl group, a furanyl group, a pyrrolyl group, an imidazolyl group, a pyrazolyl group, an isothiazolyl group, an isoxazolyl group, a thiazolyl group, an oxazolyl group, an oxadiazolyl group, a thiadiazolyl group, a triazolyl group, a phenyl group, a pyridinyl group, a pyrazinyl group, a pyrimidinyl group, a pyridazinyl group, a triazinyl group, a pentalenyl group, an indenyl group, a naphthyl group, an azulenyl group, a heptalenyl group, a biphenylenyl group, an indacenyl group, an acenaphthylenyl group, a fluorenyl group, a spiro-fluorenyl group, a carbazolyl group, an anthryl group, a phenalenyl group, a phenanthrenyl group, a perylenyl group, a fluoranthenyl group, a naphthacenyl group, a picenyl group, a pentaphenyl group, a hexacenyl group, an dibenzofuranyl group, an dibenzothiophenyl group, a phenothiazinyl group, a phenoxazinyl group, a dihydrophenazinyl group, a phenoxathiinyl group, and a phenanthridinyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —N($Q_{11}$)($Q_{12}$), wherein $Q_{11}$ and $Q_{12}$ are each independently a hydrogen atom, a $C_1$-$C_{10}$ alkyl group, a $C_6$-$C_{20}$ aryl group or a $C_2$-$C_{20}$ heteroaryl group;

$R_3$ may be one of a pentalenyl group, an indenyl group, a naphthyl group, an azulenyl group, a heptalenyl group, a biphenylenyl group, an indacenyl group, an acenaphthylenyl group, a fluorenyl group, a spiro-fluorenyl group, a carbazolyl group, an anthryl group, a phenalenyl group, a phenanthrenyl group, a perylenyl group, a fluoranthenyl group, a naphthacenyl group, a picenyl group, pentaphenyl group, a hexacenyl group, a dibenzofuranyl group, a dibenzothiophenyl group, a phenothiazinyl group, a phenoxazinyl group, a dihydrophenazinyl group, a phenoxathiinyl group, and a phenanthridinyl group; and a pentalenyl group, an indenyl group, a naphthyl group, an azulenyl group, a heptalenyl group, a biphenylenyl group, an indacenyl group, an acenaphthylenyl group, a fluorenyl group, a spiro-fluorenyl group, a carbazolyl group, an anthryl group, a phenalenyl group, a phenanthrenyl group, a perylenyl group, a fluoranthenyl group, a naphthacenyl group, a picenyl group, a pentaphenyl group, a hexacenyl group, a dibenzofuranyl group, a dibenzothiophenyl group, a phenothiazinyl group, a phenoxazinyl group, a dihydrophenazinyl group, a phenoxathiinyl group, and a phenanthridinyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —N($Q_{11}$)($Q_{12}$), wherein $Q_{11}$ and $Q_{12}$ are each independently a hydrogen atom, a $C_1$-$C_{10}$ alkyl group, a $C_6$-$C_{20}$ aryl group, or a $C_2$-$C_{20}$ heteroaryl group; and $R_6$ may be one of a cyclopropyl group, a cyclobutyl group, a cyclopentyl group, a cyclohexyl group, a cycloheptyl group, a cyclooctyl group, a cyclopentenyl group, a cyclopentadienyl group, a cyclohexenyl group, a cyclohexadienyl group, a cycloheptadienyl group, a thiophenyl group, a furanyl group, a pyrrolyl group, an imidazolyl group, a pyrazolyl group, an isothiazolyl group, an isoxazolyl group, a thiazolyl group, an oxazolyl group, an oxadiazolyl group, a thiadiazolyl group, a triazolyl group, a phenyl group, a pyridinyl group, a pyrazinyl group, a pyrimidinyl group, a pyridazinyl group, a triazinyl group, a pentalenyl group, an indenyl group, a naphthyl group, an azulenyl group, a heptalenyl group, a biphenylenyl group, an indacenyl group, an acenaphthylenyl group, a fluorenyl group, a spiro-fluorenyl group, a carbazolyl group, an anthryl group, a phenalenyl group, a phenanthrenyl group, a perylenyl group, a fluoranthenyl group, a naphthacenyl group, a picenyl group, a pentaphenyl group, a hexacenyl group, a dibenzofuranyl group, a dibenzothiophenyl group, a phenothiazinyl group, a phenoxazinyl group, a dihydrophenazinyl group, a phenoxathiinyl group, and a phenanthridinyl group; and a cyclopropyl group, a cyclobutyl group, a cyclopentyl group, a cyclohexyl group, a cycloheptyl group, a cyclooctyl group, a cyclopentenyl group, a cyclopentadienyl group, a cyclohexenyl group, a cyclohexadienyl group, a cycloheptadienyl group, a thiophenyl group, a furanyl group, a pyrrolyl group, an imidazolyl group, a pyrazolyl group, an isothiazolyl group, an isoxazolyl group, a thiazolyl group, an oxazolyl group, an oxadiazolyl group, a thiadiazolyl group, a triazolyl group, a phenyl group, a pyridinyl group, a pyrazinyl group, a pyrimidinyl group, a pyridazinyl group, a triazinyl group, a pentalenyl group, an indenyl group, a naphthyl group, an azulenyl group, a heptalenyl group, a biphenylenyl group, an indacenyl group, an acenaphthylenyl group, a fluorenyl group, a spiro-fluorenyl group, a carbazolyl group, an anthryl group, a phenalenyl group, a phenanthrenyl group, a perylenyl group, a fluoranthenyl group, a naphthacenyl group, a picenyl group, a pentaphenyl group, a hexacenyl group, an dibenzofuranyl it group, an dibenzothiophenyl group, a phenothiazinyl group, a phenoxazinyl group, a dihydrophenazinyl group, a phenoxathiinyl group, and a phenanthridinyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{60}$ alkyl, group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —N($Q_{11}$)($Q_{12}$), wherein $Q_{11}$ and $Q_{12}$ are each independently a hydrogen atom, a $C_1$-$C_{10}$ alkyl group, a $C_6$-$C_{20}$ aryl group or a $C_2$-$C_{20}$ heteroaryl group.

In some other embodiments, in Formula 1 above, $R_1$ and $R_4$ may be each independently one of a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group; a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —N($Q_{11}$)($Q_{12}$), wherein $Q_{11}$ and $Q_{12}$ are each independently a hydrogen atom, a $C_1$-$C_{10}$ alkyl group, a $C_6$-$C_{20}$ aryl group, or a $C_2$-$C_{20}$ heteroaryl group; and groups represented by Formula 2A to 2T below;

$R_2$ and $R_5$ may be each independently one of a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group; a methyl group, an ethyl group, an n-propyl group, an i-propyl group, an n-butyl group, an i-butyl group, a t-buty group, a pentyl group, a hexyl group, a heptyl group, an octyl group, a nonyl group, and a decyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —N($Q_{11}$)($Q_{12}$), wherein $Q_{11}$ and $Q_{12}$ are each independently a hydrogen atom, a $C_1$-$C_{10}$ alkyl group, a $C_6$-$C_{20}$ aryl group, or a $C_2$-$C_{20}$ heteroaryl group; groups represented by Formula 2A to 2T below; and groups represented by Formulae 3A to 3R below;

$R_3$ may be one of the groups represented by Formulae 3A to 3R; and $R_6$ may be one of Formulae 2A to 2I and Formulae 3A to 3R.

Formula 2A
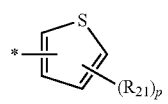
Formula 2B
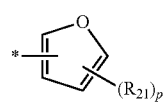
Formula 2C
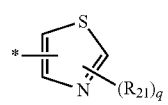
Formula 2D
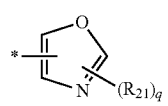
Formula 2E
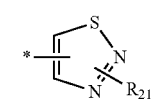
Formula 2F
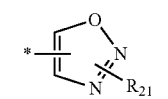
Formula 2G
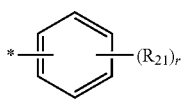
Formula 2H
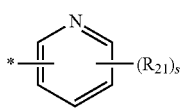
Formula 2I
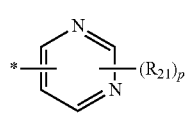
Formula 2J
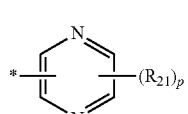
Formula 2K
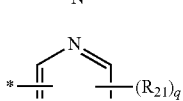
Formula 2L
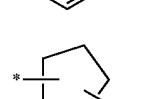
Formula 2M
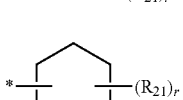
Formula 2N
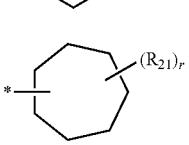
Formula 2O
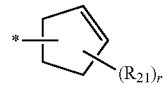
Formula 2P
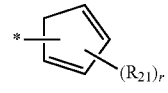
Formula 2Q
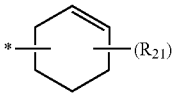
Formula 2R
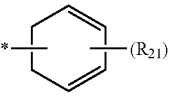
Formula 2S
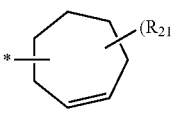
Formula 2T
Formula 3A
Formula 3B
Formula 3C
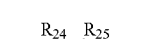
Formula 3D
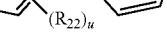
Formula 3E

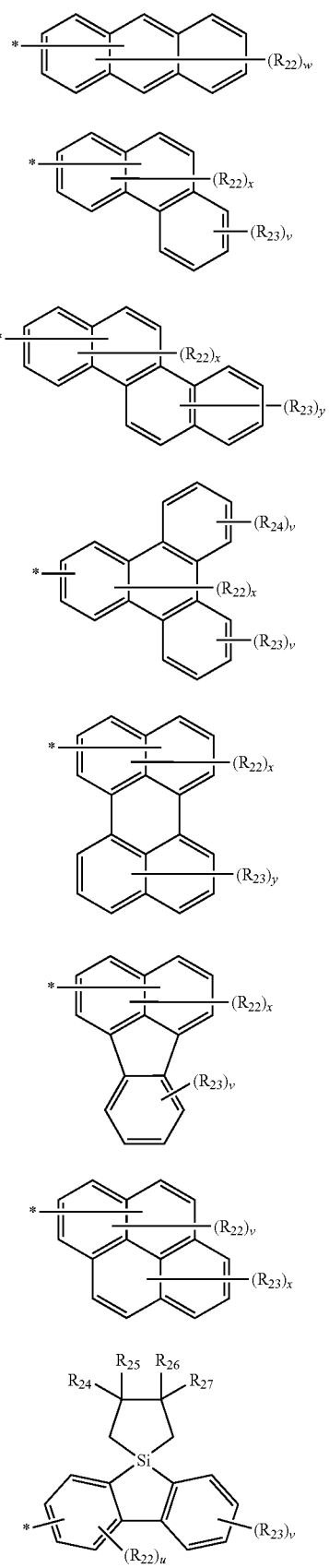

Formula 3F
Formula 3G
Formula 3H
Formula 3I
Formula 3J
Formula 3K
Formula 3L
Formula 3M

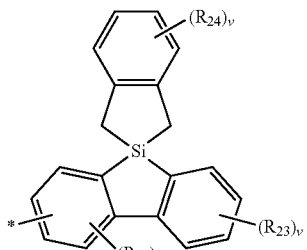

Formula 3N

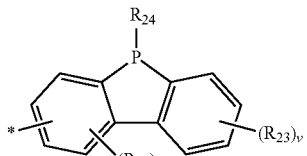

Formula 3O

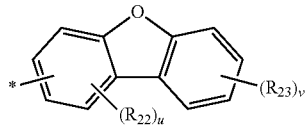

Formula 3P

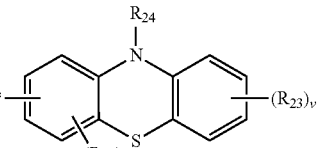

Formula 3Q

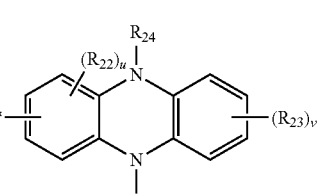

Formula 3R

In Formulae 2A to 2T and Formulae 3A to 3R, $R_{21}$ to $R_{27}$ may be each independently a hydrogen atom, a deuterium atom, a halogen atom, a hydroxyl group, a cyano group, a nitro group, an amino group, an amidino group, hydrazine, hydrazone, a carboxylic group or a salt thereof a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, or —N($Q_{21}$)($Q_{22}$), wherein $Q_{21}$ and $Q_{22}$ are each independently a hydrogen atom, a $C_1$-$C_{10}$ alkyl group, a $C_1$-$C_{20}$ aryl group, or a $C_2$-$C_{20}$ heteroaryl group; p and u may be each independently an integer from 1 to 3; q may be 1 or 2; r and x may be each independently an integer from 1 to 5; s and v may be each independently an integer from 1 to 1; t may be an integer from 1 to 7; w may be an integer from 1 to 9; and y may be an integer from 1 to 6.

If d is 2 or greater, at least two $R_{21}$ may be the same or different. This is the same as in Formulae 2B to 2T and Formulae 3A to 3R.

In Formulae 2A to 2T and Formulae 3A to 3R, $R_{21}$ to $R_{27}$ may be each independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group (for example, a methyl group, an ethyl group, an n-propyl group, an i-propyl group, an n-butyl group, an i-butyl group, a t-butyl group, a pentyl group, a hexyl group, a heptyl group, an octyl group, a nonyl group, a decyl group, and the like), a $C_2$-$C_{20}$ alkenyl group, a $C_2$-$C_{20}$ alkynyl group, a $C_1$-$C_{20}$ alkoxy group, a $C_3$-$C_8$ cycloalkyl group (for example, a cyclopropyl group, a cyclobutyl group, a cyclopentyl group, a cyclohexyl group, a cycloheptyl group, a cyclooctyl group, and the like), a $C_3$-$C_7$ cycloalkenyl group (for example, a cyclopentenyl group, a cyclopentadienyl group, a cyclohexenyl group, a cyclohexadienyl group, a cycloheptadienyl group, and the like), a $C_3$-$C_{10}$ heterocycloalkyl group, a $C_3$-$C_{10}$ heterocycloalkenyl group, a $C_6$-$C_{20}$ aryl group (for example, a phenyl group, a naphthyl group, an anthryl group, a dimethyl-fluorenyl group, a phenyl-carbazolyl group, a chrysenyl group, a pyreny group, and the like), a $C_6$-$C_{20}$ aryloxy group, a $C_6$-$C_{20}$ arylthio group, a $C_2$-$C_{20}$ heteroaryl group (for example, a pyridinyl group, a pyrimidinyl group, a pyrazolyl group, an imidazopyrimidinyl group, and the like), or —N($Q_{21}$)($Q_{22}$), wherein $Q_{21}$ and $Q_{22}$ may be each independently a hydrogen atom, a $C_1$-$C_{10}$ alkyl group, a phenyl group, a naphthyl group, or an anthryl group, but are not limited thereto.

In some other embodiments, in Formula 1 above, $R_1$ and $R_4$ may be each independently one of a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group; a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a phenyl group, a naphthyl group, and an anthryl group; and a group represented by Formula 2G;

$R_2$ and $R_5$ may be each independently one of a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group; a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a phenyl group, a naphthyl group, and an anthryl group; a group represented by Formula 2G; and groups represented by Formulae 4A to 4J;

$R_3$ may be one of the groups represented by Formulae 4A to 4J; and $R_6$ may be one of the groups represented by Formula 2G and Formulae 4A to 4J, but are not limited thereto.

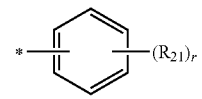

Formula 2G

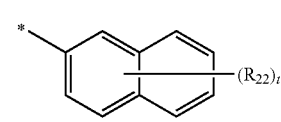

Formula 4A

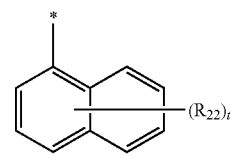

Formula 4B

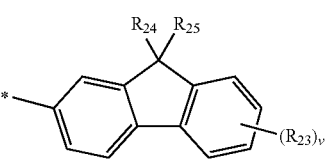

Formula 4C

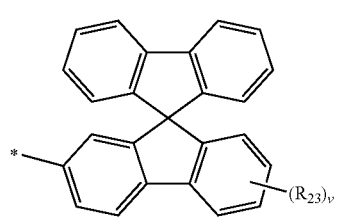

Formula 4D

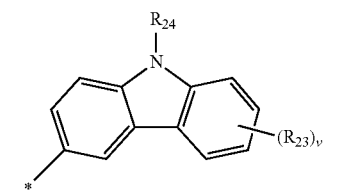

Formula 4E

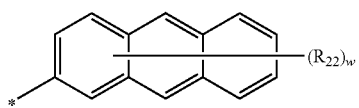

Formula 4F

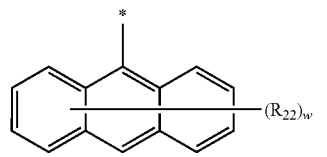

Formula 4G

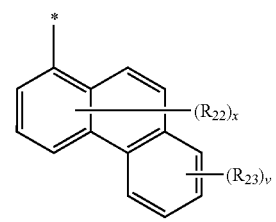

Formula 4H

-continued

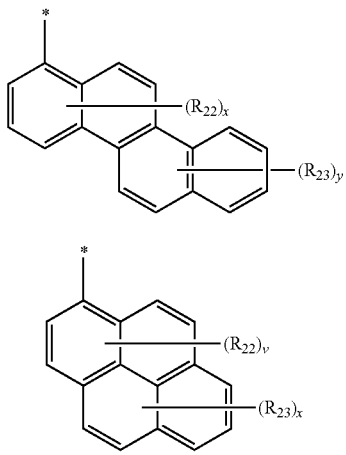

Formula 4I

Formula 4J

In Formula 2G and Formulae 4A to 4J, $R_{21}$ to $R_{25}$, r, x, v, t, w, and y may be the same as above.

In some embodiments, in Formula 20 and Formulae 4A to 4J, $R_{21}$ to $R_{25}$ may be each independently a hydrogen atom, a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof a phosphoric acid group or a salt thereof, a $C_1$-$C_{20}$ alkyl group, a $C_1$-$C_{20}$ alkoxy group, a phenyl group, a naphthyl group, an anthryl group, a dimethyl-fluorenyl group, a phenyl-carbazolyl group, a pyrenyl group, a crysenyl group, a benzothiazolyl group, a benzoxazolyl group, a phenyl-benzoimidazolyl group, or —N($Q_{21}$)($Q_{22}$), wherein $Q_{21}$ and $Q_{22}$ are each independently a hydrogen atom, a $C_1$-$C_{10}$ alkyl group, a phenyl group, a naphthyl group, or an anthryl group, but are not limited thereto.

In some other embodiments, in Formula 1 above, $R_1$ $R_2$, $R_4$, and $R_5$ may be each independently a substituted or unsubstituted $C_1$-$C_{60}$ alkyl group, or a substituted or unsubstituted non-condensed ring group having 3 to 10 ring-member atoms; $R_3$ may be a substituted or unsubstituted condensed ring group in which at least two rings are fused to each other; $R_6$ may be a substituted or unsubstituted non-condensed ring group having 3 to 10 ring-member atoms, or a substituted or unsubstituted condensed ring group in which at least two rings are fused to each other, but are not limited thereto. $R_1$ to $R_6$ may be the same as described above.

In some embodiments, in Formula 1, $R_1$ $R_2$, $R_4$, and $R_5$ may be each independently one of a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group; a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group that are substituted with at least one of a deuterium atom, a halogen, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —N($Q_{11}$)($Q_{12}$), wherein $Q_{11}$ and $Q_{12}$ are each independently a hydrogen atom, a $C_1$-$C_{10}$ alkyl group, a $C_6$-$C_{20}$ aryl group, or a $C_2$-$C_{20}$ heteroaryl group; and groups represented by Formula 2A to 2T below; $R_3$ is one of the groups represented by Formulae 3A to 3R; and $R_6$ may be one of Formulae 2A to 2T and Formulae 3A to 3R above, but are not limited thereto.

In some other embodiments, in Formula 1 above, $R_1$ $R_2$, $R_4$, and $R_5$ may be each independently a substituted or unsubstituted $C_1$-$C_{60}$ alkyl group; $R_3$ may be a substituted or unsubstituted condensed ring group in which at least two rings are fused to each other; and $R_6$ may be a 3- to 10-membered substituted or unsubstituted non-condensed ring group; or a substituted or unsubstituted condensed ring group in which at least two rings are fused to each other. $R_1$ to $R_6$ may be the same as above.

In some embodiments, in Formula 1 above, $R_1$, $R_2$, $R_4$, and $R_5$ may be each independently one of a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group; and a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —N($Q_{11}$)($Q_{12}$), wherein $Q_{11}$ and $Q_{12}$ are each independently a hydrogen atom, a $C_1$-$C_{10}$ alkyl group, a $C_6$-$C_{20}$ aryl group, or a $C_2$-$C_{20}$ heteroaryl group; $R_3$ may be one of Formulae 3A to 3R above, for example, one of Formulae 4A to 4J; $R_6$ may be one of Formulae 2A to 2T above and Formulae 3A to 3R above, for example, one of Formula 2G and Formulae 4A to 4J, but are not limited thereto.

In some other embodiments, in Formula 1 above, $R_1$, $R_2$, $R_4$, and $R_5$ may be each independently a substituted or unsubstituted $C_1$-$C_{60}$ alkyl group; $R_3$ and $R_6$ may be each independently a substituted or unsubstituted condensed ring group in which at least two rings are fused to each other.

For example, in Formula 1 above, $R_1$, $R_2$, $R_4$, and $R_5$ may be each independently one of a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group; and a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —N(Q$_{11}$)(Q$_{12}$), wherein Q$_{11}$ and Q$_{12}$ are each independently a hydrogen atom, a C$_1$-C$_{10}$ alkyl group, a C$_6$-C$_{20}$ aryl group, or a C$_2$-C$_{20}$ heteroaryl group; and R$_3$ and R$_6$ may be each independently one of Formulae 3A to 3R above, for example, one of Formulae 4A to 4J, but are not limited thereto.

In some other embodiments, in Formula 1 above, R$_1$, R$_2$, R$_4$, and R$_5$ may be each independently a substituted or unsubstituted C$_1$-C$_{60}$ alkyl group; R$_3$ may be a substituted or unsubstituted condensed ring group in which at least two rings are fused to each other; R$_6$ may be a 3- to 10-membered substituted or unsubstituted non-condensed ring group.

For example, in Formula 1 above, R$_1$, R$_2$, R$_4$, and R$_5$ may be each independently one of a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group; and a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_3$-C$_{10}$ cycloalkenyl group, a C$_3$-C$_{10}$ heterocycloalkyl group, a C$_3$-C$_{10}$ heterocycloalkenyl group, a C$_6$-C$_{60}$ aryl group, a C$_6$-C$_{60}$ aryloxy group, a C$_6$-C$_{60}$ arylthio group, a C$_2$-C$_{60}$ heteroaryl group, and —N(Q$_{11}$)(Q$_{12}$), wherein Q$_{11}$ and Q$_{12}$ are each independently a hydrogen atom, a C$_1$-C$_{10}$ alkyl group, a C$_6$-C$_{20}$ aryl group, or a C$_2$-C$_{20}$ heteroaryl group; R$_3$ may be one of the groups represented by Formulae 3A to 3R (for example, one of the groups represented by Formulae 4A to 4R; and R$_6$ may be one of Formulae 2A to 2T, for example, Formula 2G, but is not limited thereto.

In Formula 1, R$_1$ and R$_4$ may be identical to each other.
In Formula 1, R$_2$ and R$_5$ may be identical to each other.
In Formula 1. R$_3$ and R$_6$ may be identical to each other.
For example, in Formula 1, R$_1$, R$_2$, R$_4$, and R$_5$ may be identical to each other.

In some other embodiments, in Formula 1, R$_1$ R$_2$, R$_4$, and R$_5$ may be identical to each other and R$_3$ and R$_6$ may be identical to each other, but are not limited thereto.

R$_{11}$ to R$_{14}$ may be each independently a hydrogen atom, a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_3$-C$_{10}$ cycloalkenyl group, a substituted or unsubstituted C$_3$-C$_{10}$ heterocycloalkyl group, a substituted or unsubstituted C$_3$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_2$-C$_{60}$ heteroaryl group, —N(Q$_1$)(Q$_2$), or —Si(Q$_3$)(Q$_4$)(Q$_5$), wherein Q$_1$ to Q$_5$ are each independently a hydrogen atom, a C$_1$-C$_{10}$ alkyl group, a C$_6$-C$_{20}$ aryl group, or a C$_2$-C$_{20}$ heteroaryl group.

For example, in Formula 1 above, R$_1$ to R$_{14}$ may be each independently a hydrogen atom, a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof a C$_1$-C$_{20}$ alkyl group, a C$_1$-C$_{20}$ alkoxy group, a phenyl group, a naphthyl group, an anthryl group, a dimethyl-fluorenyl group, a phenyl-carbazolyl group, a pyrenyl group, or a crysenyl group, but are not limited thereto.

The cascade-type compound may be one of Compounds 1 to 22 below, but is not limited thereto.

1

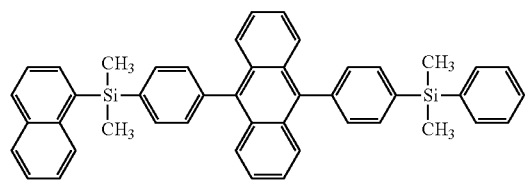

2

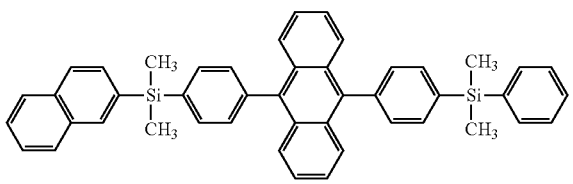

3

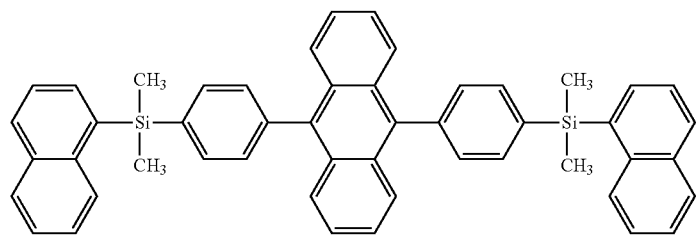

-continued
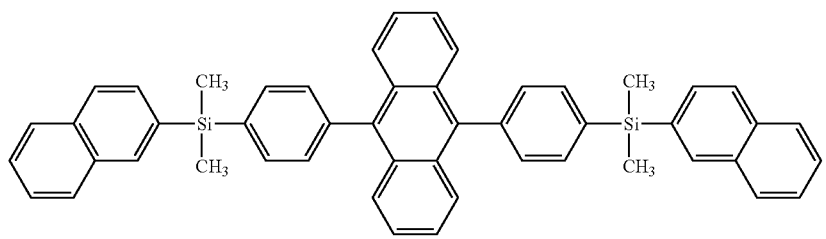
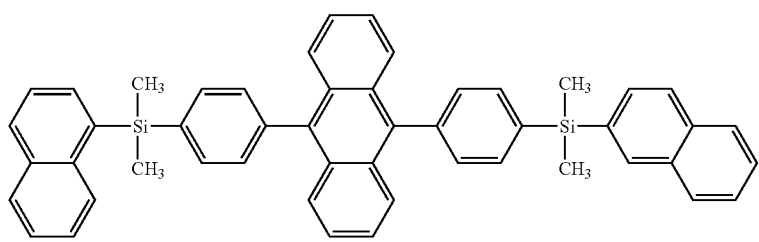
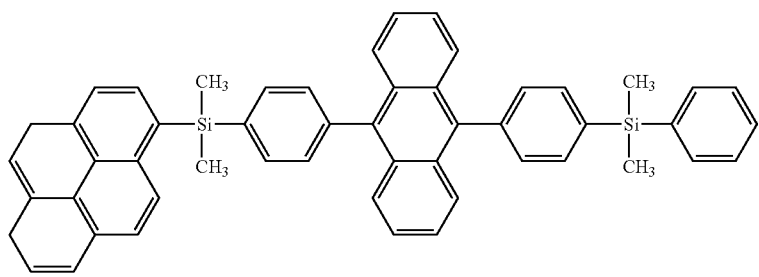
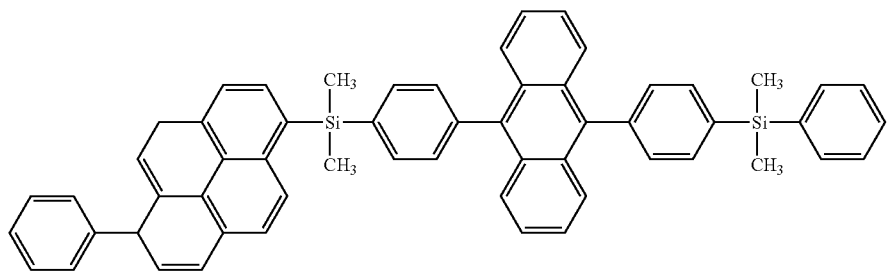
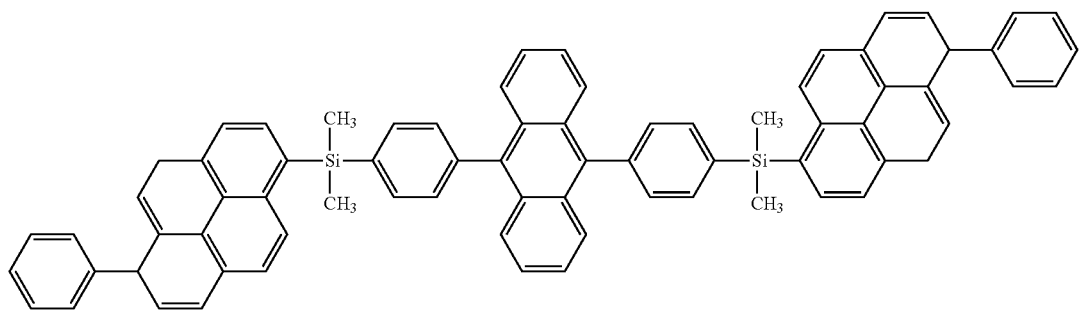
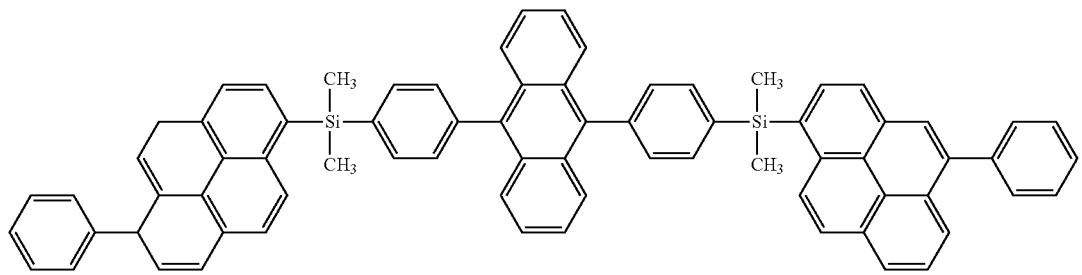

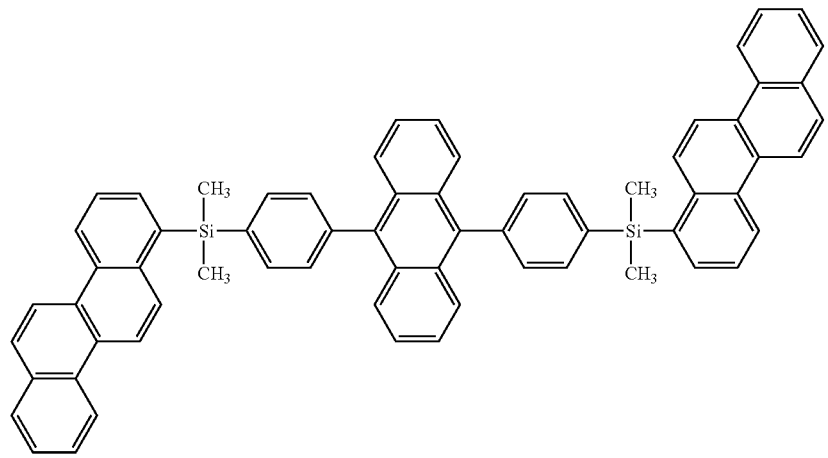
10
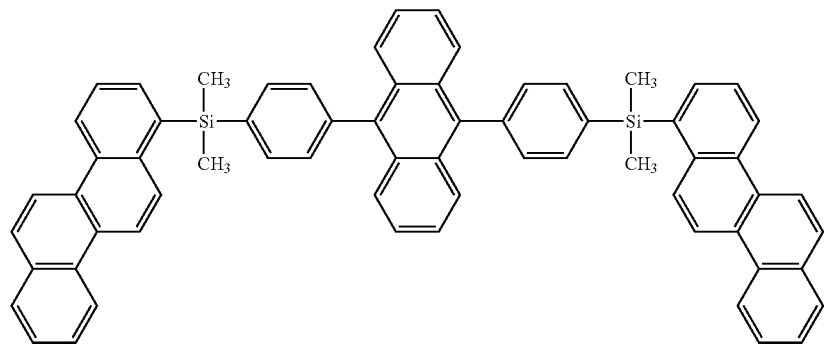
11
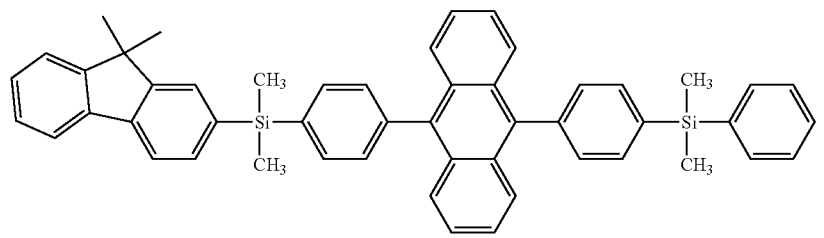
12
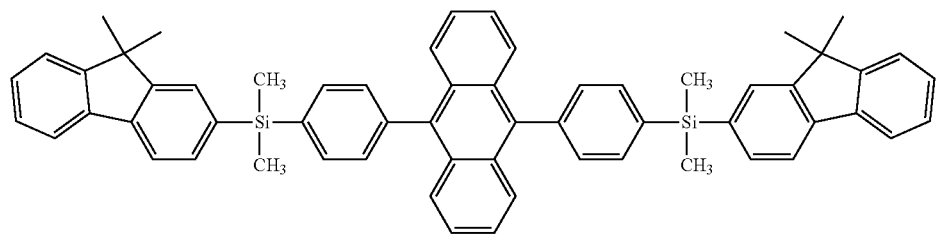
13
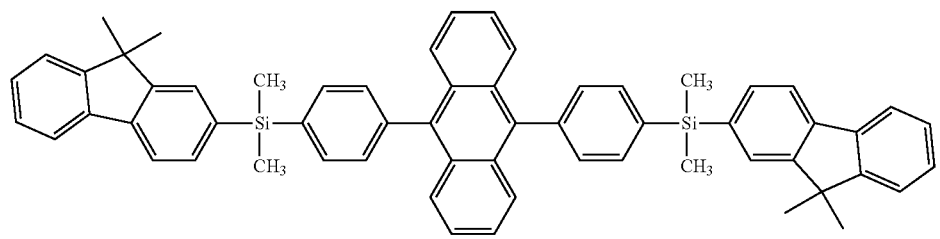
14

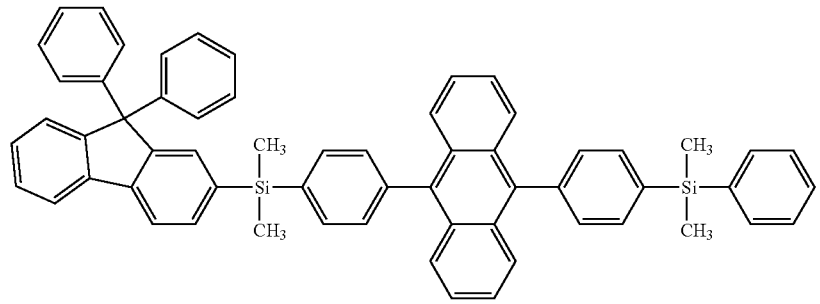
15
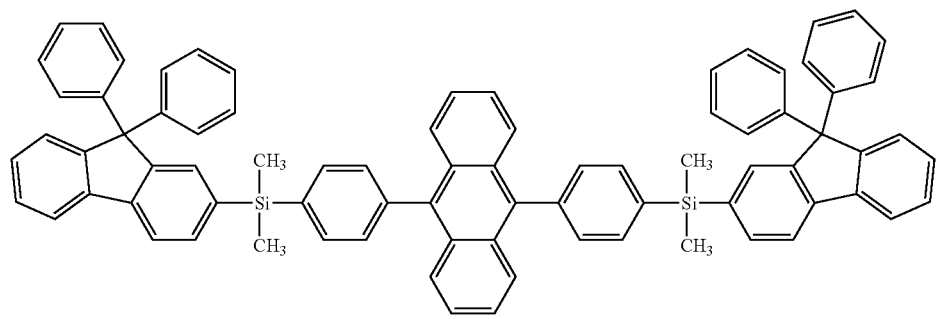
16
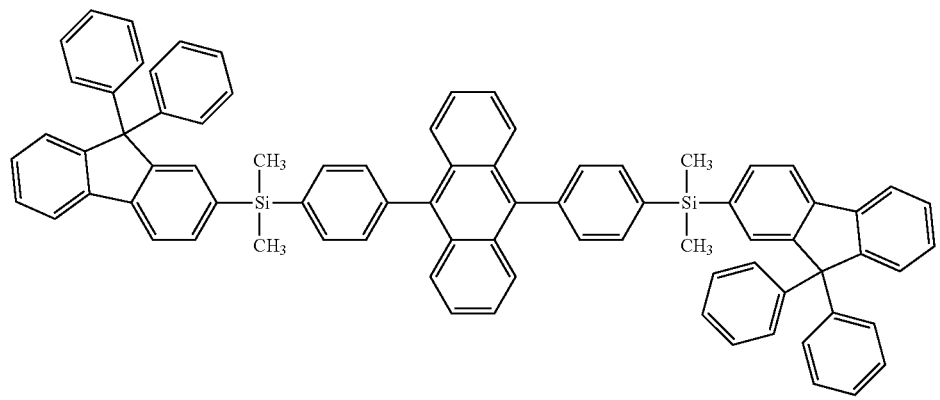
17
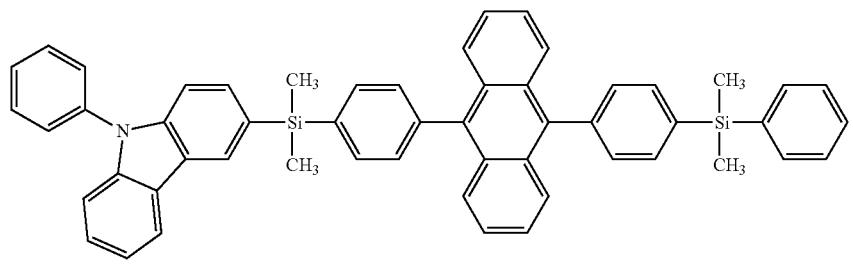
18
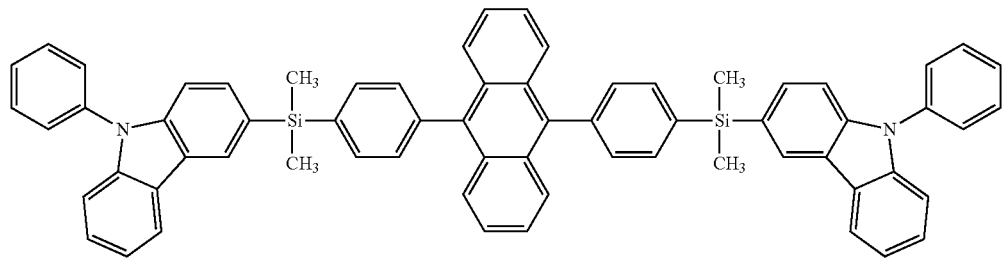
19

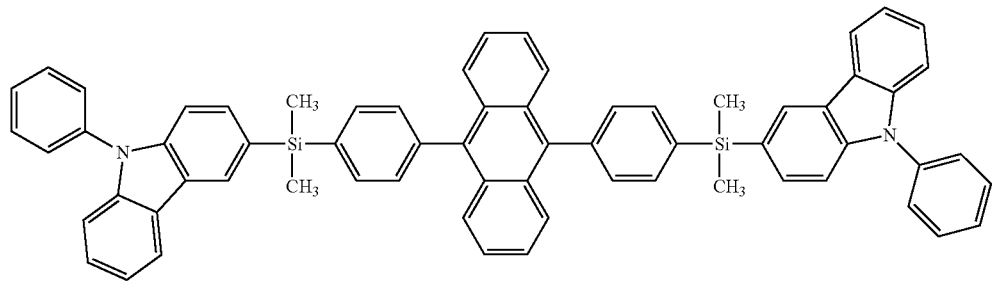

20

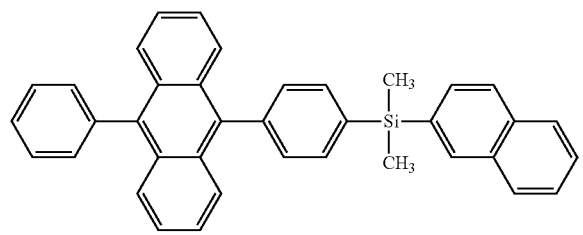

21

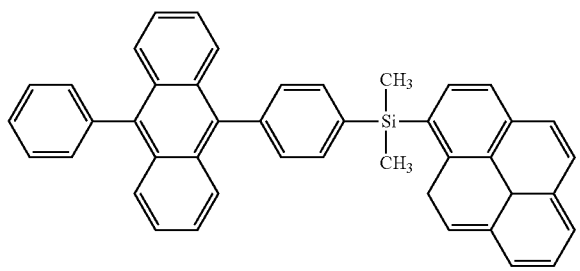

22

The cascade-type compound of Formula 1 may have high emission efficiency since $R_3$ is, or $R_3$ and $R_6$ are, "a substituted or unsubstituted condensed ring group in which at least two rings are fused to each other."

Since all $R_1$ to $R_6$ in Formula 1 above cannot be the same, steric hinderance at reaction sites of intermediates involved in the synthesis of the cascade-type compound of Formula 1 may be reduced, thus facilitating the synthesis of the cascade-type compound.

Therefore, an organic light-emitting device including the cascade-type compound represented by Formula 1 above may have a low driving voltage, a high efficiency, a high luminance, and a long lifetime.

The cascade-type compound of Formula 1 may be synthesized by using organic synthesis. A synthesis method of the cascade-type compound of Formula 1 may be understood by those of ordinary skill in the art from the examples that will be described below.

The cascade-type compound of Formula 1 may be used between a pair of electrodes of an organic light-emitting device. For example, the cascade-type compound may be used in an emission layer.

According to another aspect of the present invention, an organic light-emitting device includes a first electrode, a second electrode disposed opposite to the first electrode, and an organic layer disposed between the first electrode and the second electrode, wherein the first layer includes at least one of the cascade-type compounds of Formula 1 described above.

As used herein, "(for example, the organic layer) including at least one cascade-type compound" means "(the organic layer) including one of the cascade-type compounds of Formula above, or at least two different cascade-type compounds of Formula 1 above."

In some embodiments, the organic layer may include only Compound 1 above as the cascade-type compound. The Compound 1 may be in the emission layer of the organic light-emitting device. In some embodiments, the organic layer may include Compounds 1 and 2 as the cascade-type compound. In this regard, Compounds 1 and 2 may be used in the same layer (for example, in the emission layer).

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

The term "organic layer" as used herein refers to a single layer and/or a plurality of layers disposed between the first and second electrodes of the organic light-emitting device.

The organic layer may include an emission layer, and the emission layer may include the cascade-type of Formula 1 described above.

The cascade-type compound in the emission layer may serve as a host.

In some other embodiments, the emission layer may include only the cascade-type compound as a light-emitting material FIG. 1 is a schematic sectional view of an organic light-emitting device 10 according to an embodiment of the present invention.

Hereinafter, a structure of an organic light-emitting device according to an embodiment of the present invention and a method of manufacturing the same will now be described with reference to FIG. 1.

The substrate 11 may be any substrate that is used in existing organic light-emitting devices. In some embodiments the substrate 11 may be a glass substrate or a transparent plastic substrate with strong mechanical strength, thermal stability, transparency, surface smoothness, ease of handling, and water resistance.

The first electrode 13 may be formed by depositing or sputtering a first electrode-forming material on the substrate 11. When the first electrode 13 constitutes an anode, a material having a high work function may be used as the first electrode-forming material to facilitate hole injection. The first electrode 13 may be a reflective electrode or a transmission electrode. Suitable first electrode-forming materials include transparent and conductive materials such as ITO, IZO, $SnO_2$, and ZnO. The first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode 13 may have a single-layer structure or a multi-layer structure including at least two layers. For example, the first electrode 13 may have a three-layered structure of ITO/Ag/ITO, but is not limited thereto.

The organic layer 15 may be disposed on the first electrode 13.

The organic layer 15 may include a hole injection layer (HIL), a hole transport layer (HTL), a buffer layer, an emission layer (EML), an electron transport layer (ETL), and an electron injection layer (EIL).

The HIL may be formed on the first electrode 13 by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The HIL may be formed of any material that is commonly used to form a HIL. Non-limiting examples of the material that can be used to form the HIL are N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris(3-methylphenylphenylamino)triphenylamine (m-MTDATA), N,N'-di(1-naphthyl)-N,N-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and polyaniline)/poly(4-styrenesulfonate (PANI/PSS).

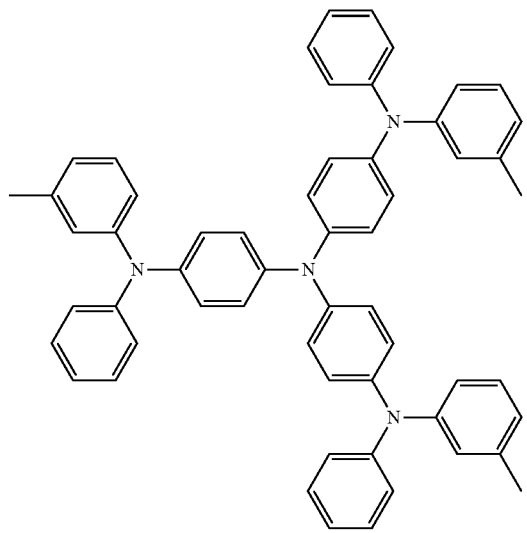

m-MTDATA

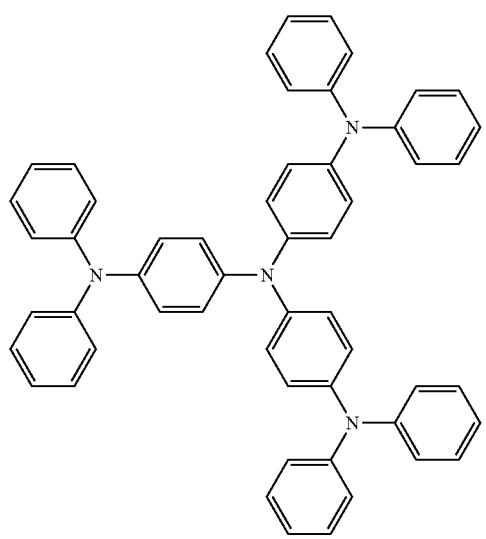

TDATA

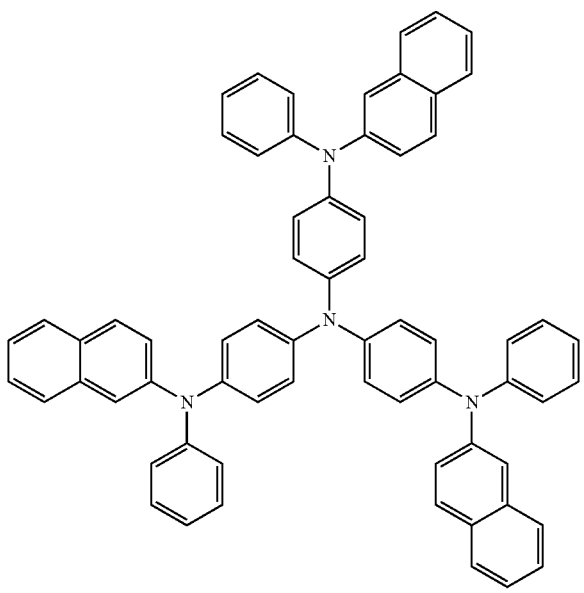

2-TNATA

The thickness of the HIL may be about 100 Å to about 10000 Å, and in some embodiments, may be from about 100 Å to about 1000 Å. When the thickness of the HIL is within these ranges, the HIL may have good hole injecting ability without a substantial increase in driving voltage.

Then, an HTL may be formed on the HIL by using vacuum deposition, spin coating, casting, Langmuir-Blodgett (LB) deposition, or the like.

When the HTL is formed using vacuum deposition or spin coating, the conditions for deposition and coating may be similar to those for the formation of the HIL, though the conditions for the deposition and coating may vary according to the material that is used to form the HTL.

Non-limiting examples of suitable known HTL forming materials are carbazole derivatives, such as N-phenylcarbazole or polyvinylcarbazole, N,N-bis(3-methylphenyl)-N,N'-diphenyl-[1,1-biphenyl]-4,4'-diamine (TPD), 4,4',4''-tris(N-carbazolyl)triphenylamine (TCTA), and N,N'-di(1-naphthyl)-N,N'-diphenylbenzidine) (NPB).

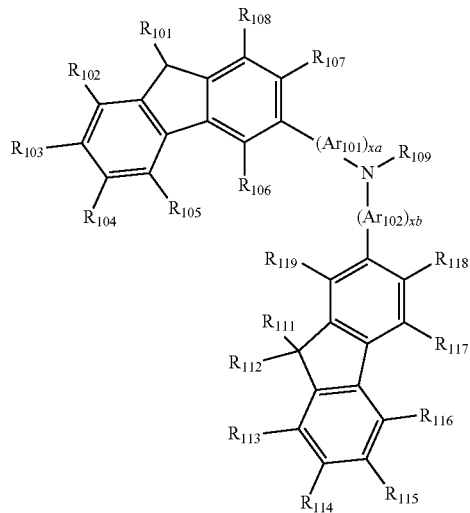

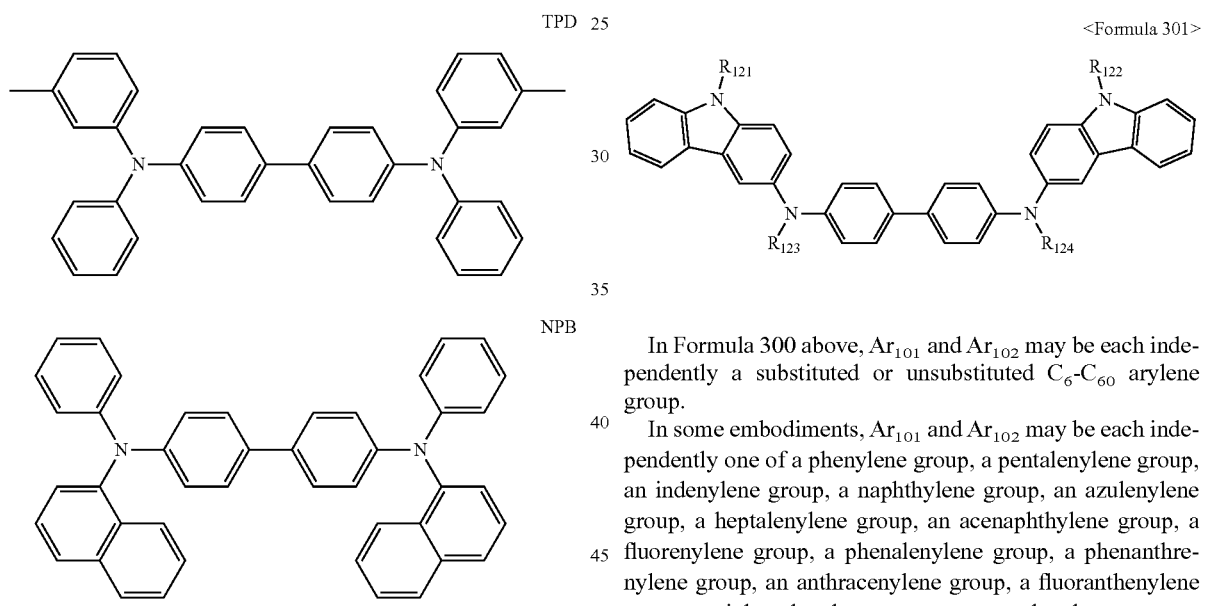

The thickness of the HTL may be from about 50 Å to about 2000 Å, and in some embodiments, may be from about 100 Å to about 1500 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10000 Å, and in some embodiments, may be from about 100 Å to about 1,000 Å. When the thickness of the H-functional layer is within these ranges, the H-functional layer may have good hole injection and transport capabilities without a substantial increase in driving voltage.

In some embodiments, at least one of the HIL, HTL, and H-functional layer may include at least one of a compound of Formula 300 below and a compound of Formula 301 below.

In Formula 300 above, $Ar_{101}$ and $Ar_{102}$ may be each independently a substituted or unsubstituted $C_6$-$C_{60}$ arylene group.

In some embodiments, $Ar_{101}$ and $Ar_{102}$ may be each independently one of a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylenylene group, a chrysenylene group, a naphthacenylene group, a picenylene group, a perylenylene group, and a pentacenylene group; and a phenylene group, a pentalenylene group, an indenylene group, a naphthylene group, an azulenyiene group, a heptalenylene group, an acenaphthylene group, a fluorenylene group, a phenalenylene group, a phenanthrenylene group, an anthracenylene group, a fluoranthenylene group, a triphenylenylene group, a pyrenylenylene group, a chrysenylene group, a naphthacenylene group, a picenylene group, a perylenylene group, and a pentacenylene group that are substituted with at least one of a deuterium atom, a halogen atom, a hydroxyl group, a nitro group, a cyano group, an amino group, an amidino group, hydrazine, hydrazone, a carboxyl group or salt thereof, a sulfuric acid or salt thereof a phosphoric acid or salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ hetero aryl group.

In Formula 300, xa and xb may be each independently an integer from 0 to 5, for example, 0, 1, or 2. For example, xa may be 1, and xb may be 0, but are not limited thereto.

In Formulae 300 and 301, $R_{101}$ to $R_{108}$, $R_{111}$ to $R_{119}$, and $R_{121}$ to $R_{124}$ may be each independently one of a hydrogen atom, a deuterium atom, a halogen atom, a hydroxyl group, a cyano group, a nitro group, an amino group, an amidino group, hydrazine, hydrazone, a carboxyl group or a salt thereof, sulfonic acid or a salt thereof, phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_2$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, and a substituted or unsubstituted $C_5$-$C_{60}$ arylthio group.

In some non-limiting embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, and a phosphoric acid or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ alkoxy group.

In Formula 300, $R_{109}$ may be each independently a phenyl group, a naphthyl group, an anthryl group, a biphenyl group, or a pyridyl group; or a phenyl group, a naphthyl group, an anthryl group, a biphenyl group, or a pyridyl group that are substituted with at least one of a deuterium atom, a halogen atom, a hydroxyl group, a cyano group, a nitro group, an amino group, an amidino group, hydrazine, hydrazone, a carboxyl group or a salt thereof, sulfonic acid or a salt thereof, phosphoric acid or a salt thereof, a substituted or unsubstituted $C_1$-$C_{20}$ alkyl group, and a substituted or unsubstituted $C_1$-$C_{20}$ alkoxy group.

In an embodiment the compound of Formula 300 may be a compound represented by Formula 300A below.

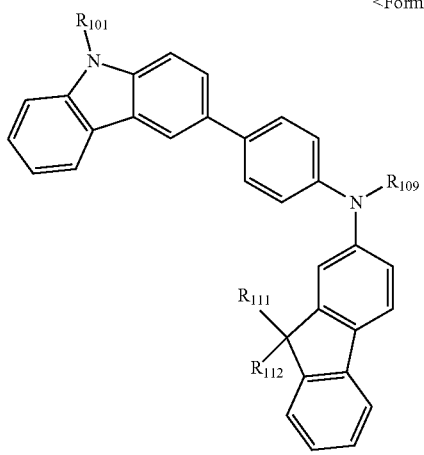

<Formula 300A>

$R_{101}$, $R_{110}$, $R_{121}$ and $R_{109}$ in Formula 300A are as defined above, and thus a detailed description thereof will not be provided here.

In some non-limiting embodiments, at least one of the HIL, HTL, and H-functional layer may include at least one of compounds represented by Formulae 301 to 320 below.

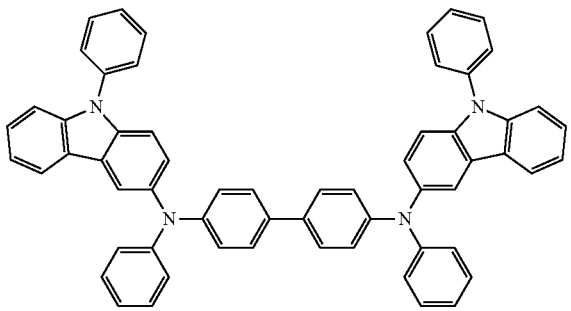

301

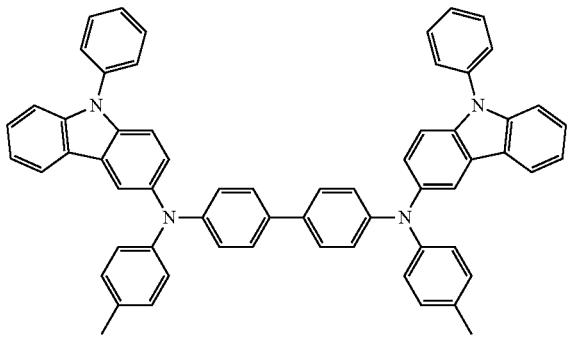

302

303
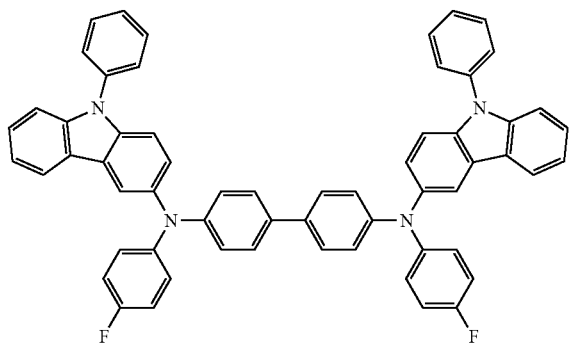
304
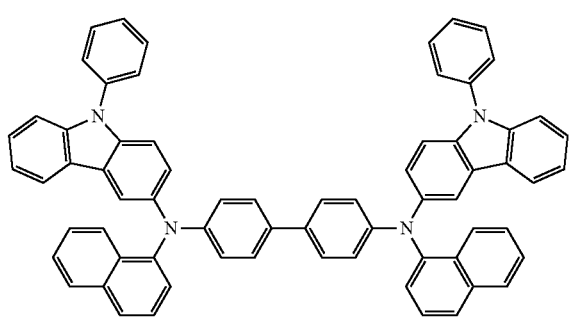
305
306
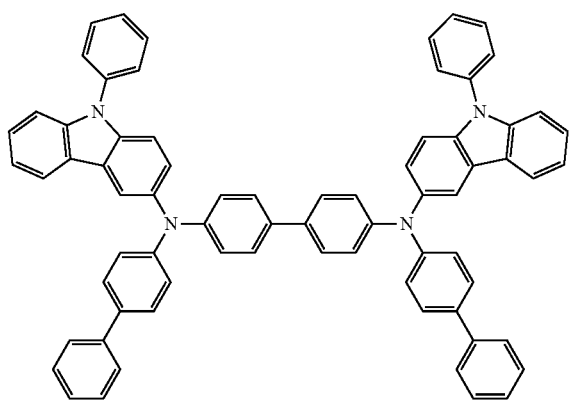
307
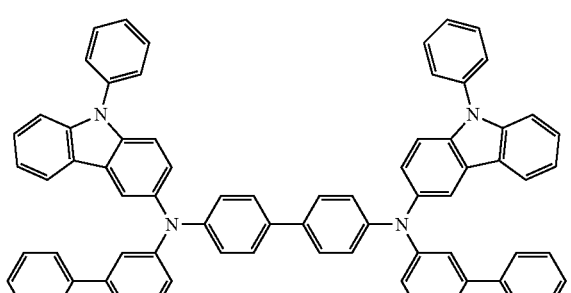
308
309
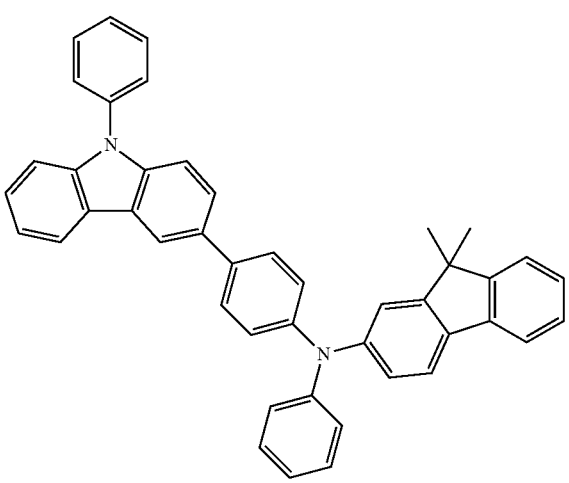

310
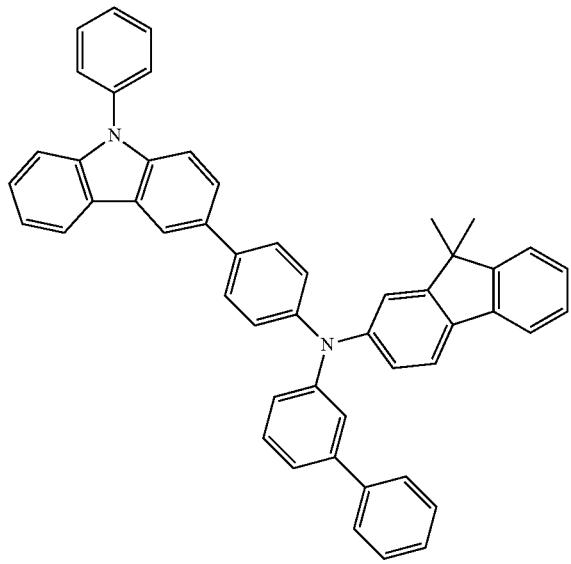
311
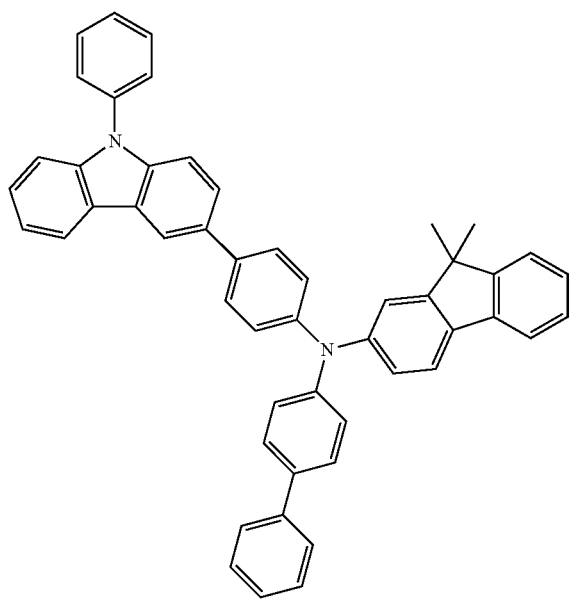
312
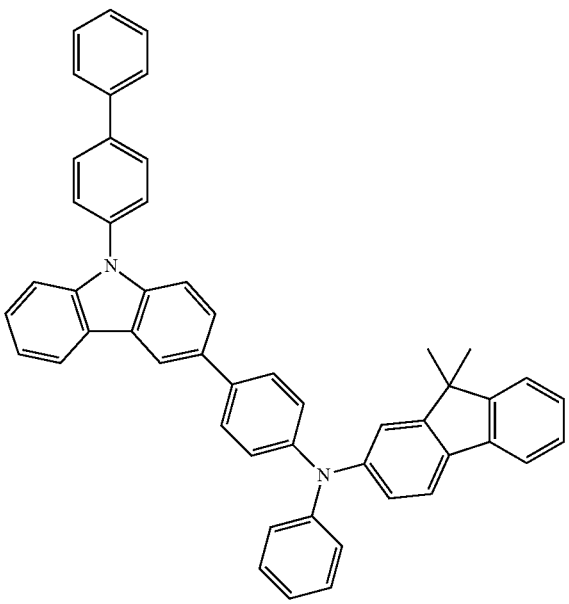
313
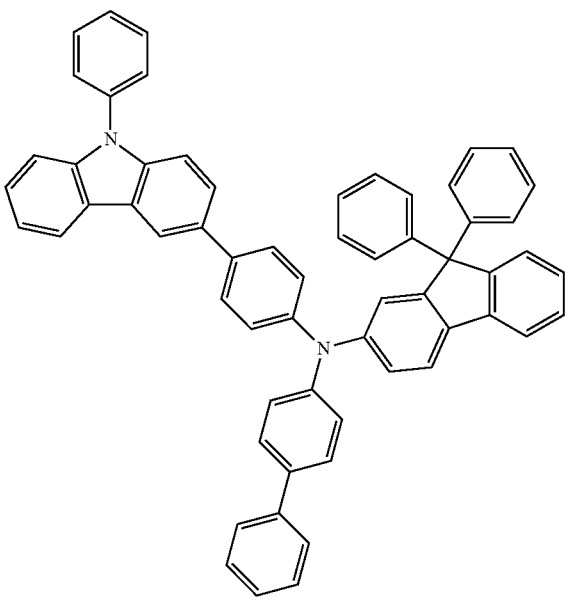

314
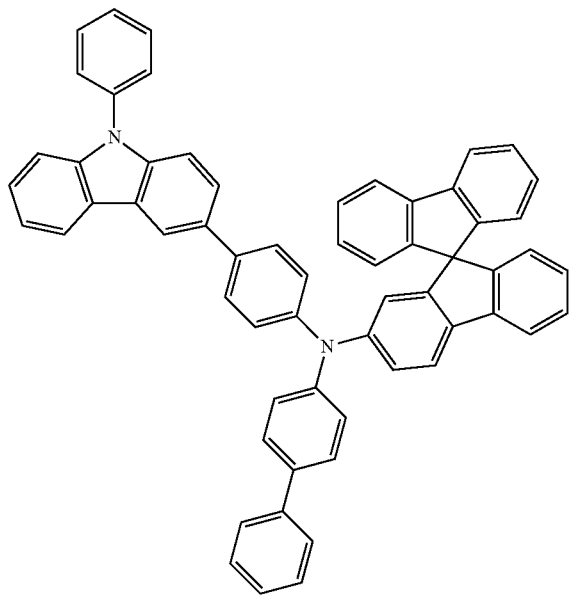
315
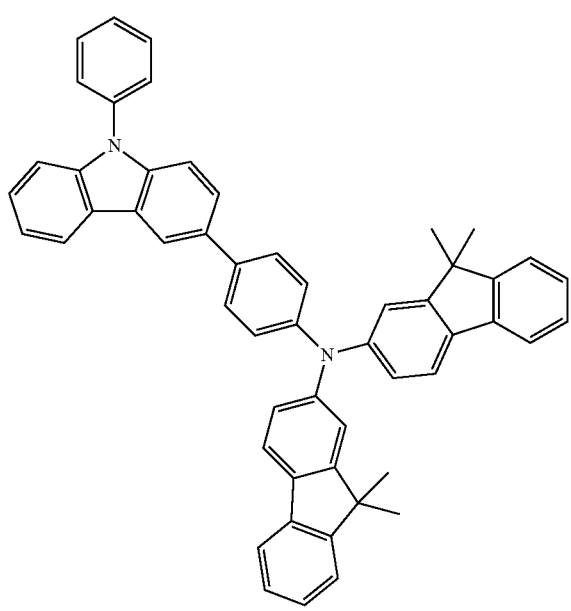
316
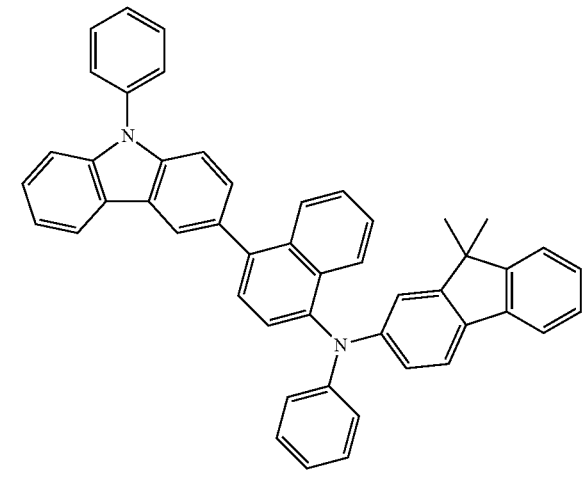
317
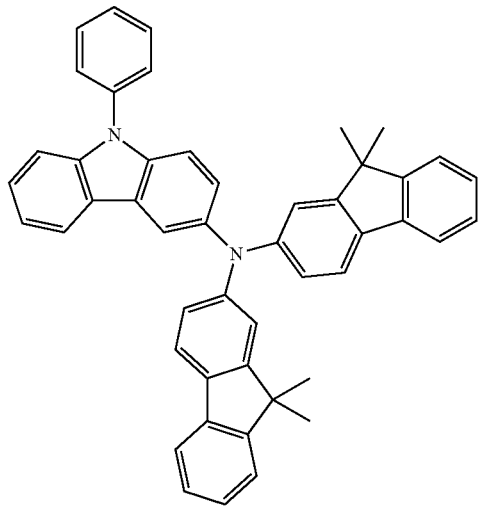
318
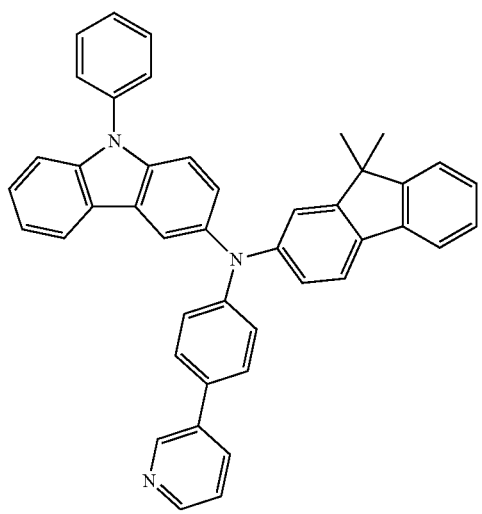

-continued

319

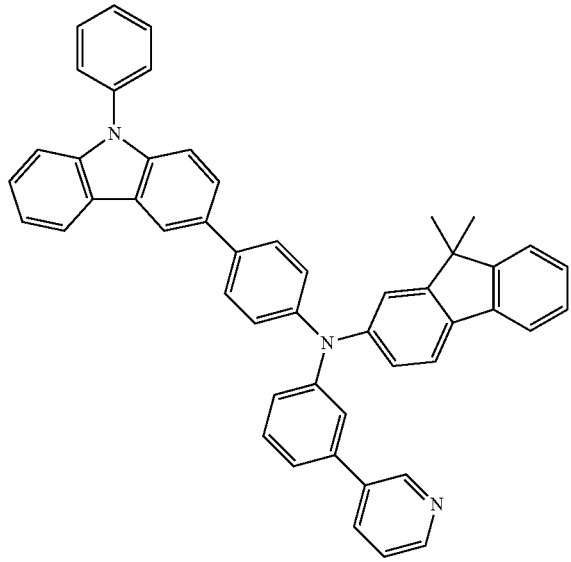

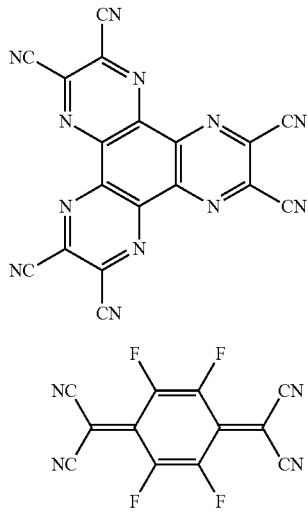

<Compound 200>

<F4-TCNQ>

320

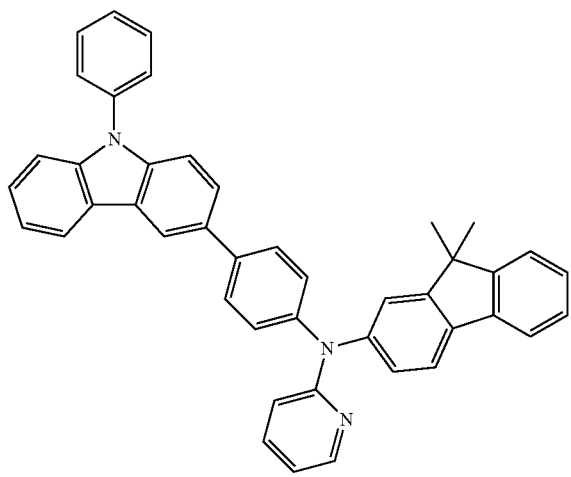

At least one of the HIL, HTL, and H-functional layer may further include a charge-generating material for improved layer conductivity, in addition to a known hole injecting material group, hole transport material group, and/or material having both hole injection and hole transport capabilities as described above.

The charge-g-generating material may be, for example, a p-dopant. The p-dopant may be one of quinine derivatives, metal oxides, and cyano group-containing compounds, but are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

When the hole injection layer, hole transport layer, or H-functional layer further includes a charge-generating material group, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The butter layer may include any hole injecting material or hole transporting material that is widely known. In some other embodiments, the buffer layer may include the same material as one of the materials included in the HIL, HTL, and H-functional layer that underlie the buffer layer.

Then, an EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The EML may include the cascade-type compound represented by Formula 1 described above. The EML may include only the cascade-type compound of Formula 1 above as a light-emitting material group, and in some embodiments, may further include at least one compound of known hosts and dopants, in addition to the cascade-type compound of Formula 1 above.

When the organic light-emitting device is a full color organic light-emitting device, the emission layer may be patterned into a red emission layer, a green emission layer, and a blue emission layer.

In some embodiments, the emission layer may include at least two of the red emission layer, the green emission layer and the blue emission layer that are stacked upon one another, and thus may emit white light.

At least one of the red EML, the green EML, and the blue EML may include a dopant is below (ppy=phenylpyridine).

Non-limiting examples of the blue dopant are compounds represented by the following formulae.

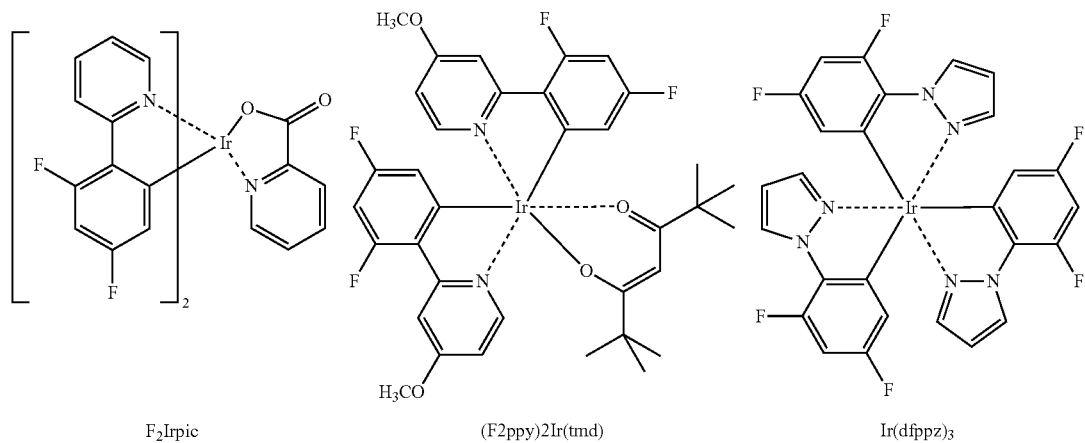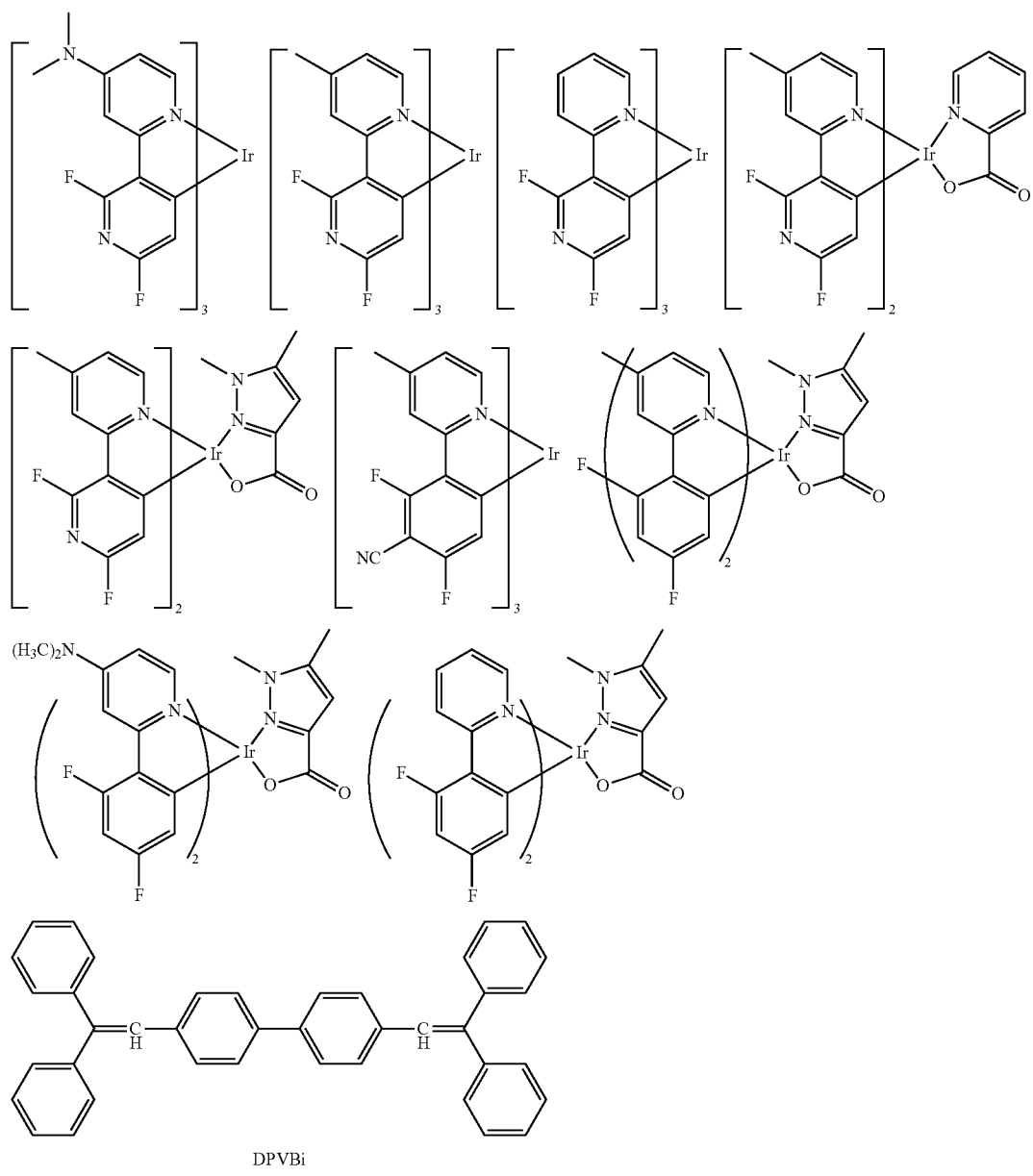

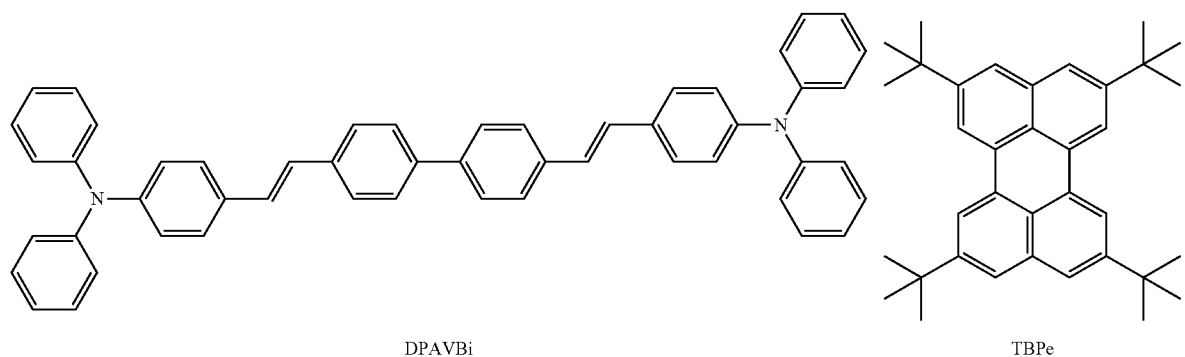
DPAVBi
TBPe
Non-limiting examples of the red dopant are compounds represented by the following formulae. In some embodiments, the red dopant may be DCM or DCJTB, which will be described later.
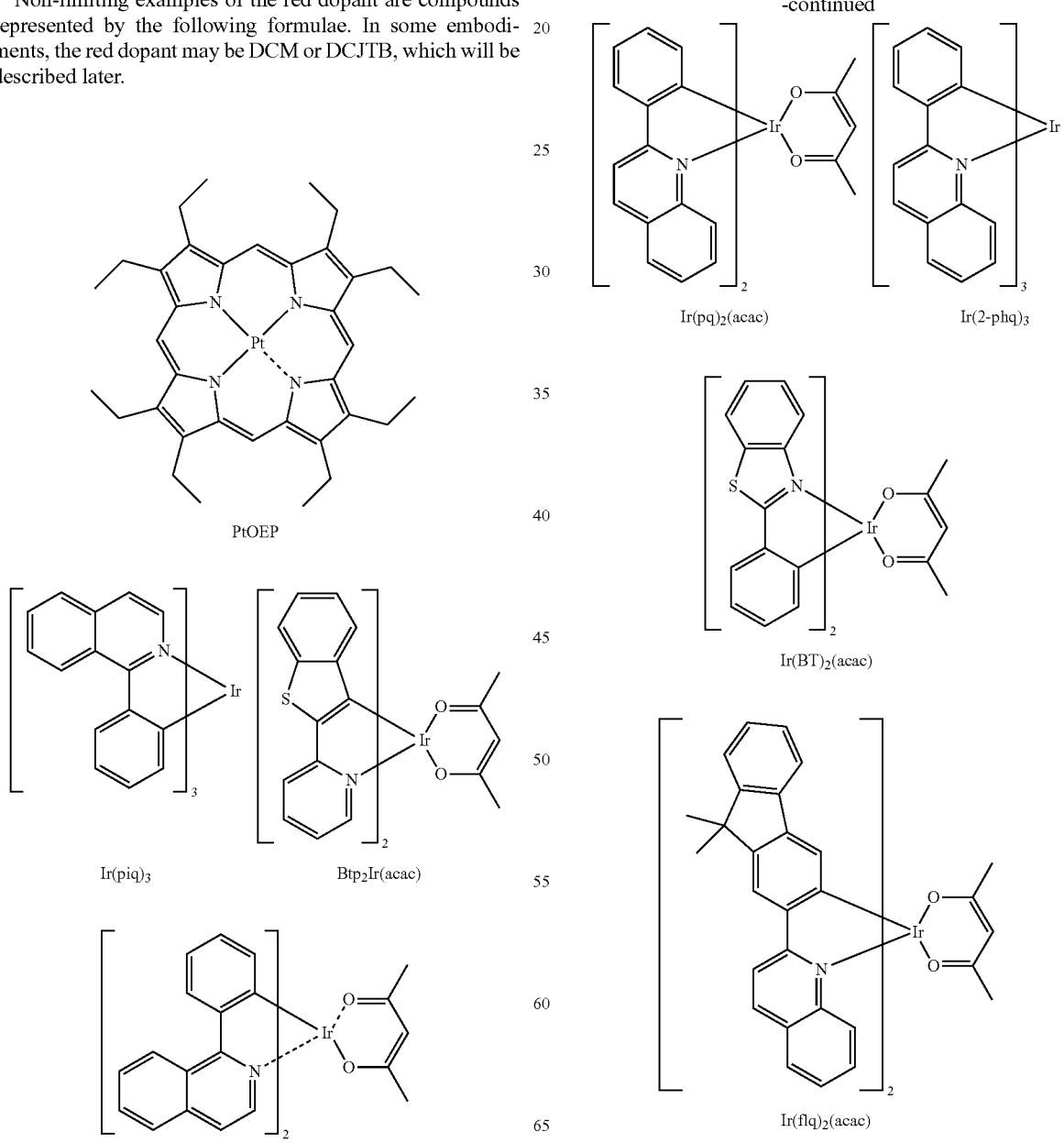
PtOEP
Ir(piq)₃
Btp₂Ir(acac)
Ir(pq)₂(acac)
Ir(2-phq)₃
Ir(BT)₂(acac)
Ir(flq)₂(acac)

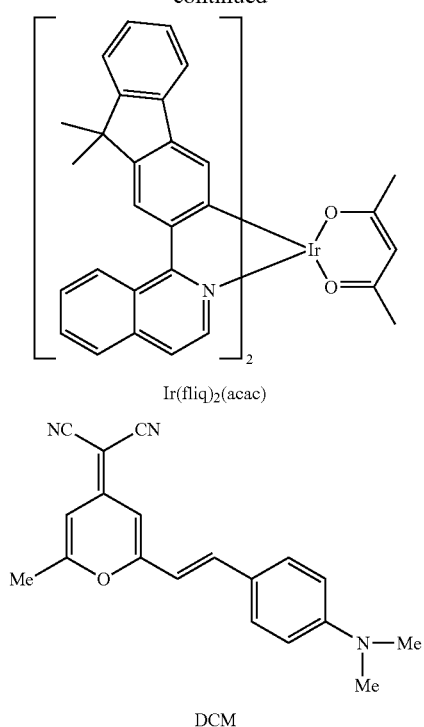

Ir(fliq)₂(acac)

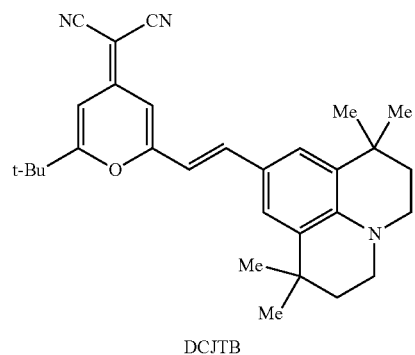 [SMILES: CC(C)(C)C1=CC(=C(C#N)C#N)C=C(/C=C/c2cc3c4c(c2)C(C)(C)CCN4CCC3(C)C)O1]

DCM

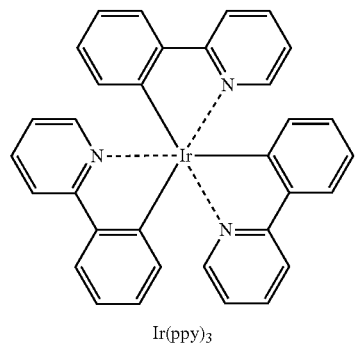

DCJTB

Non-limiting examples of the green dopant are compounds represented by the following formulae, in an embodiment, the green dopant may be C545T represented below.

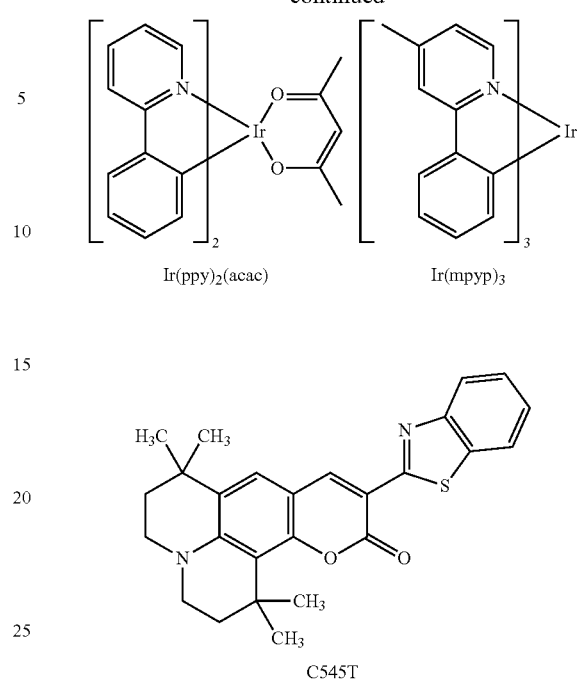

Ir(ppy)₂(acac)     Ir(mpyp)₃

C545T

When the EML includes both a host and a dopant, the amount of the dopant may be from about 0.01 to about 15 parts by weight based on 100 parts by weight of the host. However, the amount of the dopant is not limited to this range.

The thickness of the EML may be about 100 Å to about 1000 Å, and in some embodiments, may be from about 200 Å to about 600 Å. When the thickness of the EML is within these ranges, the EML may have good light emitting ability without a substantial increase in driving voltage. Then, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL. A material for forming the ETL may be any known material that can stably transport electrons injected from an electron injecting electrode (cathode). Non-limiting examples of materials for forming the ETL are a quinoline derivative, such as tris(8-quinolinorate)aluminum (Alq3), TAZ, BAlq, beryllium bis(benzoquinoline-10-olate (Bebqz), 9,10-di(naphthalene-2-yl)anthracene (ADN), Compound 201, and Compound 202, but are not limited thereto.

TAZ

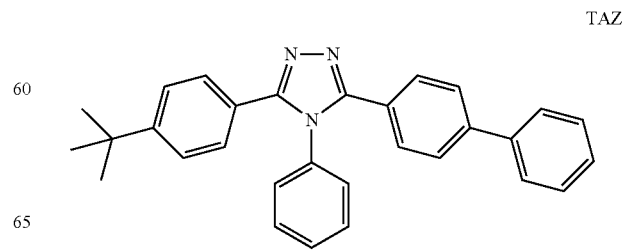

Ir(ppy)₃

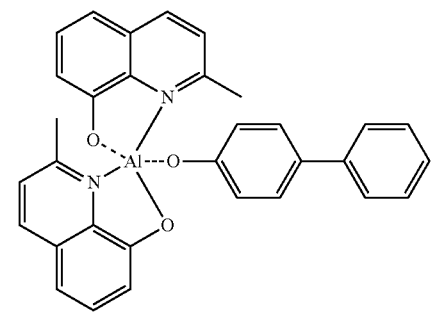

BAlq

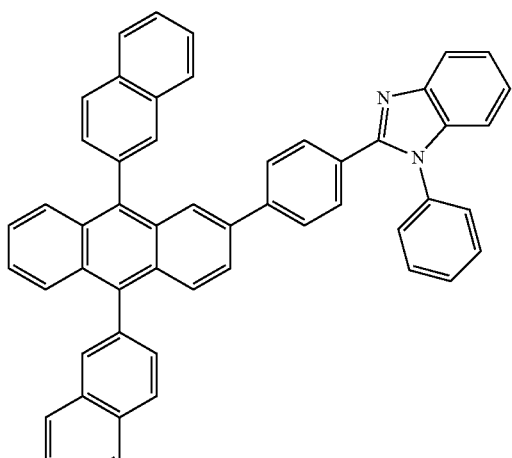

<Compound 201>

<Compound 202>

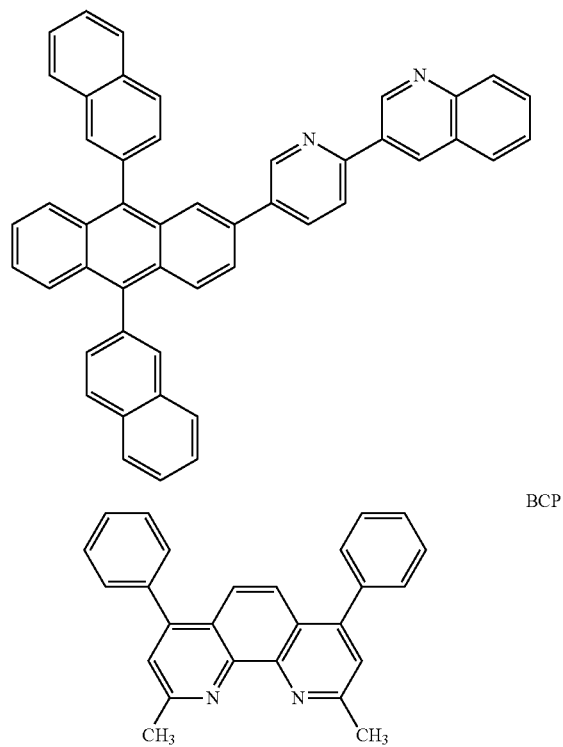

BCP

The thickness of the ETL may be from about 100 Å to about 1,000 Å, and in some embodiments, may be from about 150 Å to about 500 Å. When the thickness of the ETL is within these ranges, the ETL may have satisfactory electron transporting ability without a substantial increase in driving voltage. In some embodiments the ETL may further include a metal-containing material group, in addition to any known electron-transporting organic compound. The metal-containing material may include a lithium (Li) complex. Non-limiting examples of the Li complex are lithium quinolate (LiQ) and Compound 203 below.

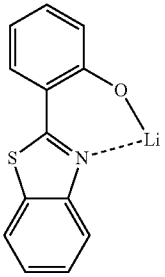

<Compound 203>

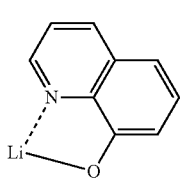

<LiQ>

Then, an EIL, which facilitates injection of electrons from the cathode, may be formed on the ETL. Any suitable electron-injecting material may be used to form the EIL. Non-limiting examples of materials for forming the EIL are LiF, NaCl group, CsF, Li$_2$O, and BaO, which are known in the art. The deposition and coating conditions for forming the EIL 18 may be similar to those for the formation of the HIL, though the deposition and coating conditions may vary according to the material that is used to form the EIL 18. The thickness of the EIL may be from about 1 Å to about 100 Å, and in some embodiments, may be from about 3 Å to about 90 Å. When the thickness of the EIL is within these ranges, the EIL may have satisfactory electron injection ability without a substantial increase in driving voltage. The second electrode 17 is disposed on the organic layer 15. The second electrode 17 may be a cathode that is an electron injection electrode. A material for forming the second electrode 17 may be a metal group, an alloy, an electro-conductive compound which has a low work function, or a mixture thereof. In this regard, the second electrode 17 may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting device, the transmission electrode may be formed of indium tin oxide (ITO) or indium zinc oxide (IZO). Although the organic light-emitting device of FIG. 1 is described above, the present invention is not limited thereto. When a phosphorescent dopant is used in the EML, an HBL may be formed between the HTL and the EML or between the H-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any known hole-blocking material may be used. Non-limiting examples of hole-blocking materials are oxadiazole derivatives, triazole derivatives, and phenanthroline derivatives. For example, bathocuproine (BCP), represented by the following formula, may be used as a material for forming the HBL.

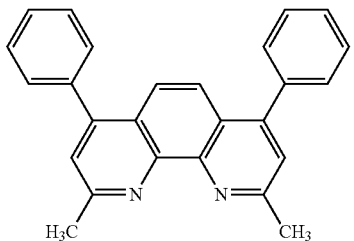

BCP

The thickness of the HBL may be from about 20 Å to about 1000 Å, and in some embodiments, may be from about 30 Å to about 300 Å. When the thickness of the HBL is within these ranges, the HBL may have improved hole blocking ability without a substantial increase in driving voltage. Hereinafter, the present invention will be described in detail with reference to the following Synthesis Examples and other Examples. However, these Examples are for illustrative purposes only and are not intended to limit the scope of the present invention. Examples of the unsubstituted $C_1$-$C_{60}$ alkyl group used herein are linear or branched $C_1$-$C_{60}$ alkyl groups, such as a methyl group, an ethyl group, a propyl group, an isobutyl group, a sec-butyl group, a pentyl group, an iso-amyl group, a hexyl group, or the like. In the substituted $C_1$-$C_{60}$ alkyl group, at least one hydrogen atom of the unsubstituted $C_1$-$C_{60}$ alkyl group described above is substituted with a deuterium atom, a halogen atom, a hydroxyl group, a nitro group, a cyano group, an amino group, an amidino group, a hydrazine, a hydrazone, a carboxyl group or salts thereof, a sulfonic acid group or salts thereof, a phosphoric acid group or salts thereof, a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, —N($Q_{11}$)($Q_{12}$), or —Si($Q_{13}$)($Q_{14}$)($Q_{15}$), wherein $Q_1$ to $Q_{15}$ may be each independently selected from the group consisting of a hydrogen atom, a $C_1$-$C_{60}$ alkyl group, a $C_2$-$C_{60}$ alkenyl group, a $C_2$-$C_{60}$ alkynyl group, a $C_5$-$C_{60}$ aryl group, and a $C_2$-$C_{60}$ heteroaryl group. The unsubstituted $C_1$-$C_{60}$ alkoxy group may be a group represented by —OA, wherein A is an unsubstituted $C_1$-$C_{60}$ alkyl group described above. Examples of the unsubstituted $C_1$-$C_{60}$ alkoxy group are a methoxy group, an ethoxy group, and an isopropyloxy group. At least one of the hydrogen atoms in the alkoxy group may be substituted with the substituents described above in conjunction with the substituted $C_1$-$C_{60}$ alkyl group. As used herein, the unsubstituted $C_2$-$C_{60}$ alkenyl group is a hydrocarbon chain having a carbon-carbon double bond in the center or at a terminal of the unsubstituted $C_2$-$C_{60}$ alkyl group. Examples of the unsubstituted $C_2$-$C_{60}$ alkenyl group are an ethenyl group, a propenyl group, and a butenyl group. At least one hydrogen atom in the unsubstituted $C_2$-$C_{60}$ alkenyl group may be substituted with the substituents described in conjunction with the substituted $C_1$-$C_{60}$ alkyl group. The unsubstituted $C_2$-$C_{60}$ alkynyl group is a hydrocarbon chain having at least one carbon-carbon triple bond in the center or at a terminal thereof. Examples of the unsubstituted $C_2$-$C_{60}$ alkynyl group are an ethenyl group, a propenyl group, a butenyl group, and the like. At least one hydrogen atom in the alkynyl group may be substituted with the substituents described above in conjunction with the $C_1$-$C_{60}$ alkyl group. The unsubstituted $C_6$-$C_{60}$ aryl group is a monovalent group having a carbocyclic aromatic system having 6 to 60 carbon atoms including at least one aromatic ring. The unsubstituted $C_6$-$C_{60}$ arylene group is a bivalent group having a carbocyclic aromatic system having 6 to 60 carbon atoms including at least one aromatic ring. When the aryl group and the arylene group have at least two rings, they may be fused to each other via a single bond. At least one hydrogen atom in the aryl group and the arylene group may be substituted with the substituents described above in conjunction with the $C_1$-$C_{60}$ alkyl group. Examples of the substituted or unsubstituted $C_6$-$C_{60}$ aryl group are a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group and a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene) phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an to anthracenyl group, an azulenyl group, a heptalenyl group, an acenaphthylenyl group, a phenalenyl group, a fluorenyl group, an anthraquinonyl group, a methylanthryl group, a phenanthryl group, a triphenylenyl group, a pyrenyl group, a chrysenyl group, an ethylchrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and an ovalenyl group. Examples of the substituted $C_5$-$C_{60}$ aryl group may be inferred based on those of the unsubstituted $C5$-$C_{60}$ aryl group and the substituted $C_1$-$C_{60}$ alkyl group described above. Examples of the substituted or unsubstituted $C_5$-$C_{60}$ arylene group may be inferred based on those examples of the substituted or unsubstituted $C_5$-$C_{60}$ aryl group described above. The unsubstituted $C_2$-$C_{10}$ heteroaryl group is a monovalent group having at least one aromatic ring having at least one of the heteroatoms selected from the group consisting of N, O, P, and S. The unsubstituted $C_2$-$C_{60}$ heteroarylene group is a divalent group having at least one aromatic ring having at least one of the heteroatoms selected from the group consisting of N, O, P, and S. In this regard, when the heteroaryl group and the heteroarylene group have at least two rings, they may be fused to each other via a single bond. At least one hydrogen atom in the heteroaryl group and the heteroarylene group may be substituted with those substituents described above in conjunction with the $C_1$-$C_{60}$ alkyl group. Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group and an imidazopyrimidinyl group. Examples of the unsubstituted $C_2$-$C_{60}$ heteroarylene group may be inferred based on those examples of the substituted or unsubstituted $C_2$-$C_{60}$ arylene group described above. The substituted or unsubstituted $C_6$-$C_{60}$ aryloxy group indicates —OA$_2$ (wherein A$_2$ is a substituted or unsubstituted $C_6$-$C_{60}$ aryl group described above). The substituted or unsubstituted $C_5$-$C_{10}$ arylthio group indicates —SA$_3$ (wherein A$_3$ is a substituted or unsubstituted $C_6$-$C_{60}$ aryl group described above).

Generally speaking, the term "substituted", when used in conjunction with a functional group or compound, unless otherwise defined, means that the functional group or compound can be substituted with a deuterium atom, a halogen atom, a hydroxyl group, a nitro group, a cyano group, an, amino group, an amidino group, a hydrazine, a hydrazone, a carboxyl group or salts thereof, a sulfonic acid group or salts thereof, a phosphoric acid group or salts thereof, a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, —N($Q_{11}$)

($Q_{12}$), or —Si($Q_{13}$)($Q_{14}$)($Q_{15}$), wherein $Q_1$ to $Q_{15}$ is may be each independently selected from the group consisting of a hydrogen atom, a $C_1$-$C_{60}$ alkyl group, a $C_2$-$C_{60}$ alkenyl group, a $C_2$-$C_{60}$ alkynyl group, a $C_1$-$C_{60}$ aryl group, and a $C_2$-$C_{60}$ heteroaryl group.

EXAMPLES

Synthesis Example 1

Synthesis of Compound 2

<Synthesis of Compound 2-1>

Reaction Scheme 2-1

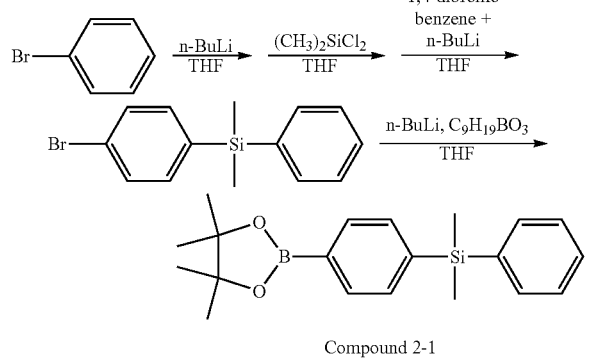

Compound 2-1

After 12 g (58.25 mmol) of 1-bromobenzene was dissolved in 200 ml of THF in a 500-ml 3-necked round flask (flask 1) in a nitrogen atmosphere, 23.65 ml (58.25 mmol) of 2.5M n-BuLi was slowly dropped into the solution at −78° C. and stirred for about 20 minutes while the temperature was maintained. Afterward, 6.93 g (54.17 mmol) of dimethyldichlorosilane was very slowly dropwise added into the mixture at −80° C. or less, and the temperature was slowly increased to about −10° C. or less, at which the mixture was further stirred for about 2 hours. After 18.97 g (80.39 mmol) of 1,4-dibromobenzene was dissolved in 200 ml of THF in a 250-ml 3-necked round flask (flask 2) in a nitrogen atmosphere, 32.63 ml (80.39 mmol) of n-BuLi was slowly dropped into the solution at −78° C. and stirred for about 20 minutes while the temperature was maintained. While the temperatures of the reaction products in flasks 1 and 2 were maintained at about −78° C. the reaction product in flask 2 was taken using a syringe, dropwise added into flask 1, and then stirred for about 12 hours. After termination of the reaction using water, the reaction product was extracted using chloroform and purified using a silica gel column equipped with hexane eluent, and then recrystallized using hexane to obtain (4-bromo-phenyl)-dimethyl-phenyl-1-yl-silane. After (4-bromo-phenyl)-dimethyl-phenyl-1-yl-silane and 250 ml of THF were put in a 500-ml 3-necked round flask, 14.21 ml (35 mmol) of 2.5M n-BuLi was slowly dropped into the solution at −78° C. and stirred for about 40 minutes while the temperature was maintained. Afterward, 6.55 g (35 mmol) of 2-isopropoxy-4,4,5,5,-tetramethyl-1,3,2-dioxaborane was slowly added into the mixture at −78° C. or less and stirred for about 30 minutes, and then further stirred for about 12 hours after the temperature was slowly increased. After termination of the reaction with 10% HCl group, the reaction product was extracted using ethylacetate. An extracted organic layer was collected and purified using a silica gel column equipped with hexane eluent, and then recrystallized using ethylacetate and hexane to obtain 3.94 g (12.65 mmol) of a white solid Compound 2-1

(Yield: 20%). 1H NMR (300 MHz, CDCl3) δ; 7.85 (2H), 7.55 (1H), 7.46 (4H), 7.37 (2H), 1.24 (12H), 0.66 (6H).

<Synthesis of Compound 2-2>

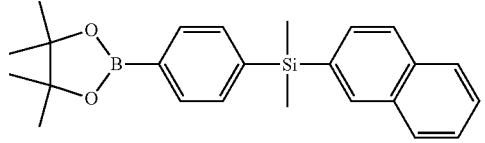

Compound 2-2

Compound 2-2 was synthesized in the same manner as in the synthesis of Compound 2-1, except that 2-bromonaphthalene, instead of 1-bromobenzene, was used (white solid, Yield: 22%). 1H NMR (300 MHz, CDCl3) δ; 8.10 (1H), 8.00 (2H), 7.95 (1H), 7.85 (2H), 7.60 (1H), 7.59 (21H), 7.46 (2H), 1.24 (12H), 0.66 (611).

<Synthesis of Compound 2>

Reaction Scheme 2

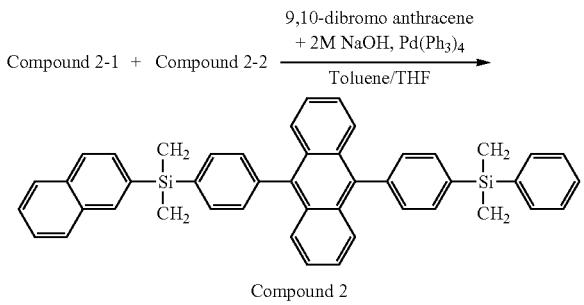

Compound 2

After 5 g (14.79 mmol) of Compound 2-1, 5.74 g (14.79 mmol) of Compound 2-2, and 4.28 g (12.86 mmol) of 9,10-dibromoanthracene were added to 300 ml of toluene in a 250-ml 3-necked flask with an addition of 100 ml of 2M NaOH and reacted for about 30 minutes for nitrogen substitution, a catalytic amount of tetrakis(triphenylphosphine)palladium(0) was added thereto and reacted at about 100° C. for about 36 hours. After termination of the reaction with the HCl group, the reaction product was filtrated, washed several times with acetone, and then dried. The resulting product was subjected to soxhlet extraction with toluene to obtain Compound 2 (white solid, 4.10 g, 6.36 mmol group, Yield: 43%). 1H NMR (300 MHz, CDCl3) δ; 8.10 (1H), 8.00 (2H), 7.95 (1H), 7.91 (4H), 7.89 (4H), 7.60 (1H), 7.59 (2H), 7.55 (1H), 7.52 (4H), 7.46 (2H), 7.39 (4H), 7.37 (2H), 0.66 (12H). HRMS (FAB); calcd for C46H36Si2; 644.24. found; 644.95, Synthesis Example 2

Synthesis of Compound 6

<Synthesis of Compound 6-1>

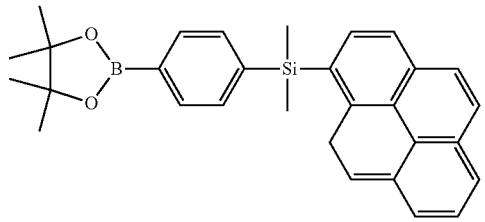

Compound 6-1

Compound 6-1 was synthesized in the same manner as in the synthesis of Compound 2-1, except that 1-bromopyrene, instead of i-bromobenzene, was used (white solid, Yield: 20%). 1H NMR (300 MHz, CDCl3) δ; 7.91 (II), 7.85 (1H), 7.81 (1H), 7.46 (2H), 7.17 (1H), 7.10 (1H), 6.58 (1H), 6.44 (1H), 6.19 (1H), 6.00 (1H), 1.24 (12H), 0.66 (6H).

<Synthesis of Compound 6>

Compound 6

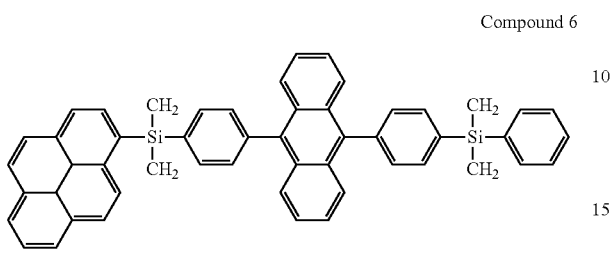

Compound 6 was synthesized in the same manner as in the synthesis of Compound 2, except that Compound 6-1, instead of Compound 2-2, was used (Yield: 41%). 1H NMR (300 MHz, CDCl3) δ; 7.98 (9H), 7.91 (4H), 7.89 (2H). 7.79 (2H), 7.55 (1H), 7.52 (2H), 7.46 (2H), 7.39 (4H), 7.37 (2H), 7.24 (2H), 4.82 (2H), 0.66 (12H). HRMS (FAB); calcd for C52H40Si2; 720.27. found; 721.04.

Synthesis Example 3

Synthesis of Compound 13

<Synthesis of Compound 13-1>

Compound 13-1

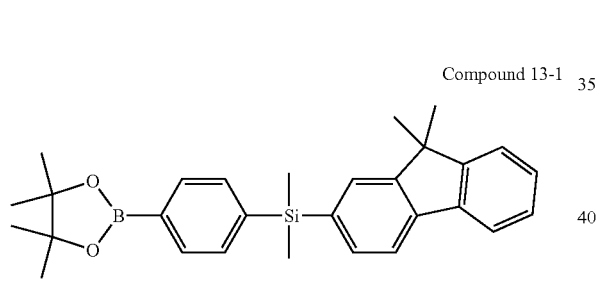

Compound 13-1 was synthesized in the same manner as in the synthesis of Compound 2-1, except that 2-bromo-(9,9-dimethyl)fluorene, instead of 1-bromobenzene, was used (white solid, Yield: 18%) 1H NMR (300 MHz, CDCl3) δ; 7.97 (1H), 7.87 (1H), 7.85 (2H), 7.83 (1H), 7.66 (1H), 7.55 (1H), 7.46 (2H), 7.38 (1H), 7.28 (1H), 1.72 (6H), 1.24 (12H), 0.66 (6H), <Synthesis of Compound 13>

Compound 13 was synthesized in the same manner as in the synthesis of Compound 2, except that Compound 13-1, instead of Compound 2-1 and Compound 2-2, was used (Yield: 38%), 1H NMR (300 MHz, CDCl3) δ; 7.97 (2H), 7.91 (4H), 7.89 (4H), 7.87 (2H), 7.83 (2H), 7.66 (2H), 7.55 (2H), 7.52 (4H), 7.39 (4H), 7.38 (2H), 7.28 (2H), 1.72 (12H) 0.66 (12H). HRMS (FAB); calcd for C60H50Si2; 826.35. found; 827.21.

Synthesis Example 4

Synthesis of Compound 19

<Synthesis of Compound 19-1>

Compound 19-1

Compound 19-1 was synthesized in the same manner as in the synthesis of Compound 2-1, except that 3-bromo-(9-phenyl)carbazole, instead of 3-bromobenzene, was used (white solid, Yield: 20%). 1H NMR (300 MHz, CDCl3) δ; 8.55 (1H), 7.94 (1H), 7.85 (2H), 7.83 (1H), 7.73 (1H). 7.58 (2H), 7.50 (2H) 7.46 (2H), 7.45 (1H), 7.36 (1H), 733 (1H), 7.25 (1H), 1.24 (12H), 0.66 (6H).

Compound 13

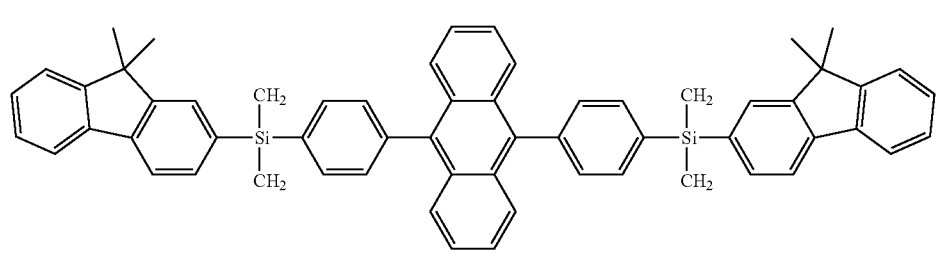

<Synthesis of Compound 19>

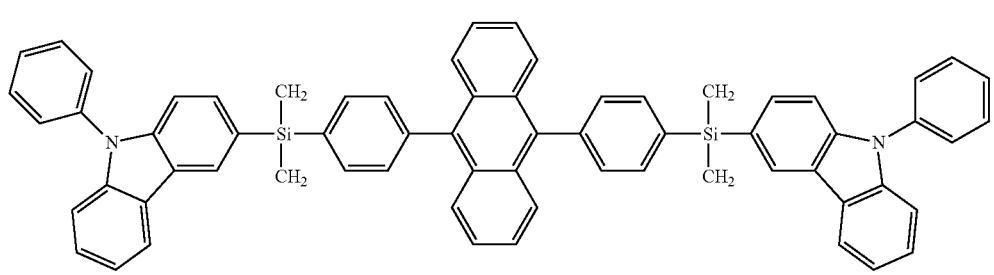

Compound 19

Compound 19 was synthesized in the same manner as in the synthesis of Compound 2, except that Compound 19-1, instead of Compound 2-1 and Compound 2-2, was used (Yield: 39%). 1H NMR (300 MHz, CDCl3) δ; 8.55 (2H), 7.94 (2H), 7.91 (4H), 7.89 (4H), 7.83 (2H), 7.73 (2H), 7.58 (4H), 7.52 (4H), 7.50 (4H), 7.45 (2H) 7.39 (4H), 7.36 (2H) 7.33 (2), 7.25 (2H) 0.66 (12H). HRMS (FAB); Compound C66H48N2Si2; 924.34. found; 925.27.

Synthesis Example 5

Synthesis of Compound 22

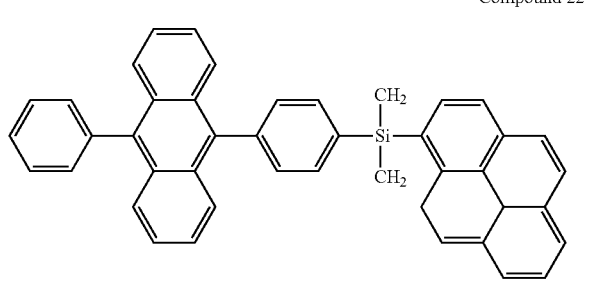

Compound 22

Compound 22 was synthesized in the same manner as in the synthesis of Compound 2, except that 10-bromo-9-phenylanthracene, instead of 9,10-dibromoanthracene was used, Compound 6-1, instead of Compound 2-1, was used, and Compound 2-2 was not used (Yield: 47%), 1H NMR (300 MHz, CDCl3) δ; 7.98 (6H), 7.91 (4H), 7.79 (2H), 7.39 (4H), 7.24 (2H), 5.34 (1H), 3.22 (2H), 2.05 (6H), 0.66 (6H). HRMS (FAB): calcd for C44H32Si: 588.23. found: 588.81.

Example 1

A corning 15 Ω/cm² (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

2-TNATA was deposited on the ITO layer as an anode to form an HIL having a thickness of 600 Å on the anode, and then 4.4'-bis[N-(1-naphthyl)-N-phenylamino]biphenyl (NPS) was deposited on the HIL to form an HTL having a thickness of 300 Å.

Compound 2 as a blue fluorescent material was deposited on the HTL to form an EML having a thickness of about 400 Å.

Then, Compound 201 was deposited on the EML to form an ETL having a thickness of about 300 Å, and then LiF was deposited on the ETL to form an EIL having a thickness of about 10 Å. Then, Al was deposited on the EIL to form a second electrode (cathode) having a thickness of about 3000 Å, thereby completing the manufacture of an organic light-emitting device.

A driving voltage, luminescence and efficiency of the organic light-emitting device were measured using Kethley SMU 236 at a current density of 10 mA/cm². As a result, the organic light-emitting device was found to have a driving voltage of 4.3 V, a luminescence of 275 cd/m², and an efficiency of 2.75 cd/A.

Example 2

An organic light-emitting device was manufactured in the same manner as in Example 1, except that Compound 6, instead of Compound 2, was used to form the EML.

A driving voltage, luminosity and efficiency of the organic light-emitting device were measured using Kethley SMU 236 at a current density of 10 mA/cm². As a result, the organic light-emitting device was found to have a driving voltage of 4.5 V, a luminescence of 378 cd/m², and an efficiency of 3.78 cd/A.

Example 3

An organic light-emitting device was manufactured in the same manner as in Example 2, except that Compound 13, instead of Compound 2, was used to form the EML.

A driving voltage, luminosity and efficiency of the organic light-emitting device were measured using Kethley SMU 236 at a current density of 10 mA/cm². As a result, the organic light-emitting device was found to have a driving voltage of 3.9 V, a luminescence of 335 cd/m², and an efficiency of 3.35 cd/A.

Example 4

An organic light-emitting device was manufactured in the same manner as in Example 1, except that Compound 19, instead of Compound 2, was used to form the EML.

A driving voltage, luminosity and efficiency of the organic light-emitting device were measured using Kethley SMU 236 at a current density of 10 mA/cm². As a result, the organic light-emitting device was found to have a driving voltage of 3.8 V, a luminescence of 345 cd/m², and an efficiency of 3.45 cd/A.

Example 5

An organic light-emitting device was manufactured in the same manner as in Example 1, except that Compound 22, instead of Compound 2, was used to form the EML.

A driving voltage, luminosity and efficiency of the organic light-emitting device were measured using Kethley SMU 236 at a current density of 10 mA/cm². As a result, the organic light-emitting device was found to have a driving voltage of 4.4 V, a luminescence of 365 cd/m², and an efficiency of 3.65 cd/A.

Comparative Example 1

An organic light-emitting device was manufactured in the same manner as in Example 1, except that Compound A, instead of Polymer 2, was used to form the EML.

A driving voltage, luminosity and efficiency of the organic light-emitting device were measured using Kethley SMU 236 at a current density of 10 mA/cm². As a result, the organic light-emitting device was found to have a driving voltage of 4.7 V, a luminescence of 143 cd/m², and an efficiency of 1.43 cd/A.

<Compound A>

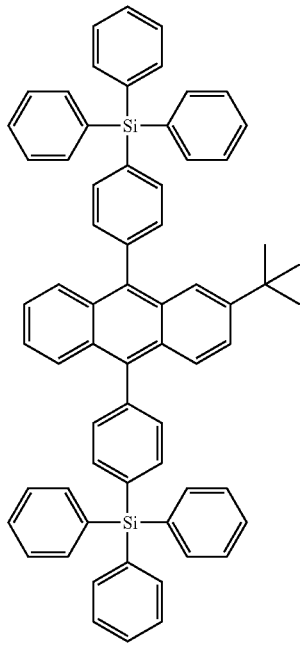

The characteristics of the organic light-emitting devices of Examples 1 to 5 and Comparative Example 1 are summarized in Table 1 below. Color purity was measured using Kethley SMU 236, and T95 lifetime indicates the time taken until an initial luminescence (assumed to be 100%) measured at a current density of about 10 mA/cm² is reduced to 95%.

Referring to Table 1, the organic light-emitting devices of Examples 1 to 5 are found to have lower driving voltages, higher luminescence, higher efficiencies, improved lifetime characteristics, and improved color purity characteristics, as compared with the organic light-emitting device of Comparative Example 1.

As described above, an organic light-emitting device including any of the cascade-type compounds according to the embodiments of the present invention may have a low driving voltage, a high efficiency, and a long lifetime, While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A cascade-type compound represented by Formula 1:

<Formula 1>

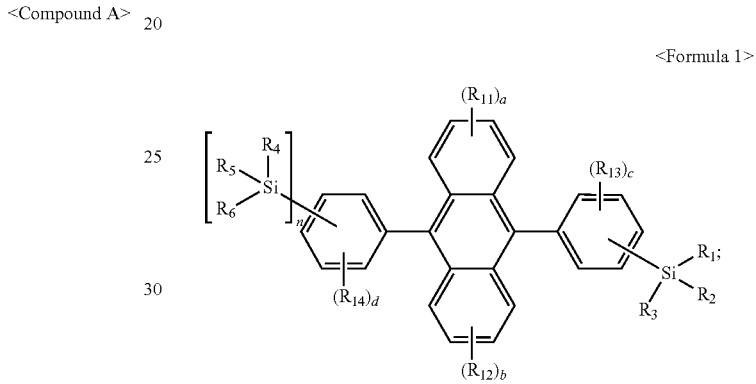

in Formula 1:

n is 0 or 1;

$R_1$, $R_2$, $R_4$ and $R_5$ are each independently a substituted or unsubstituted $C_1$-$C_{60}$ alkyl group;

$R_3$ is a substituted or unsubstituted condensed ring group in which at least two rings are fused to each other;

$R_6$ is a 3- to 10-membered substituted or unsubstituted non-condensed ring group $R_{11}$ to $R_{14}$ are each independently a hydrogen atom, a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or

TABLE 1

| | EML material | Driving voltage (V) | Current density (mA/cm²) | Luminescence (cd/m²) | Efficiency (cd/A) | CIE x | CIE y | T95 lifetime (hr) |
|---|---|---|---|---|---|---|---|---|
| Example 1 | Compound 2 | 4.3 | 10 | 275 | 2.75 | 0.145 | 0.093 | 120 |
| Example 2 | Compound 6 | 4.5 | 10 | 378 | 3.78 | 0.143 | 0.112 | 160 |
| Example 3 | Compound 13 | 3.9 | 10 | 335 | 3.35 | 0.151 | 0.102 | 130 |
| Example 4 | Compound 19 | 3.8 | 10 | 345 | 3.45 | 0.152 | 0.104 | 140 |
| Example 5 | Compound 22 | 4.4 | 10 | 365 | 3.65 | 0.144 | 0.114 | 150 |
| Comparative Example1 | Compound A | 4.7 | 10 | 143 | 1.43 | 0.147 | 0.091 | 60 | unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —N($Q_1$)($Q_2$), or —Si($Q_3$)($Q_4$)($Q_5$), wherein $Q_1$ to $Q_5$ are each independently a hydrogen atom, a $C_1$-$C_{10}$ alkyl group, a $C_6$-$C_{20}$ aryl group, or a $C_2$-$C_{20}$ heteroaryl group;

a, b and c are each independently an integer from 1 to 4; and d is an integer from 1 to 5, provided that a compound where n is 1 and all of $R_3$ and $R_6$ are unsubstituted pyrenyl groups is excluded.

2. The cascade-type compound of claim 1, wherein the cascade-type compound is represented by one of Formulae 1A to 1F below:

<Formula 1A>

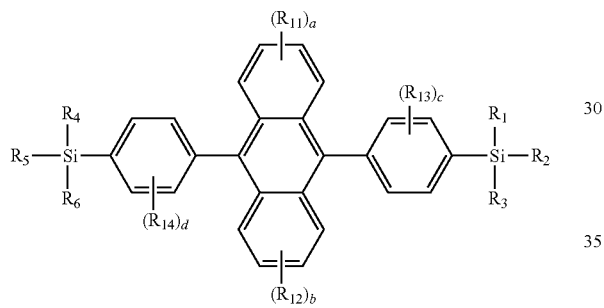

<Formula 1B>

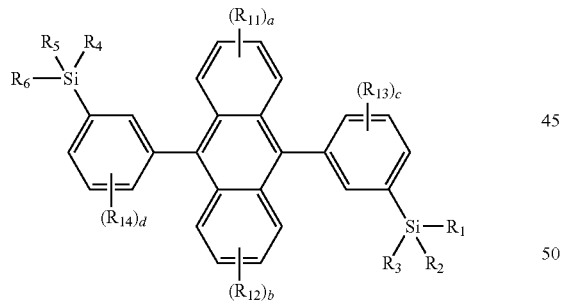

<Formula 1C>

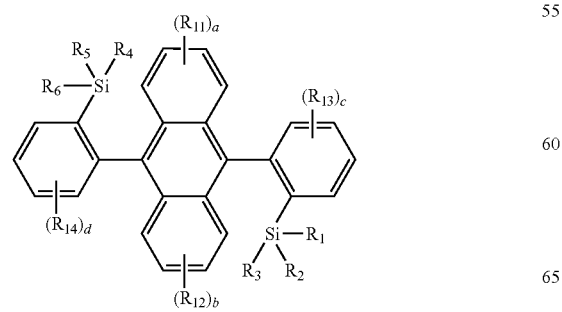

<Formula 1D>

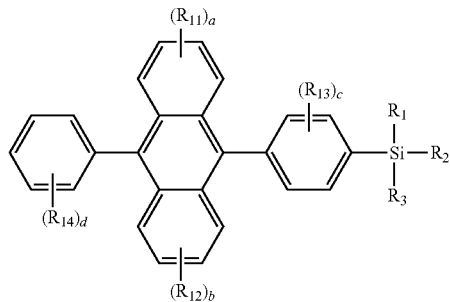

<Formula 1E>

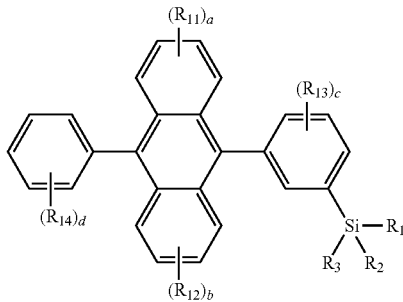

<Formula 1F>

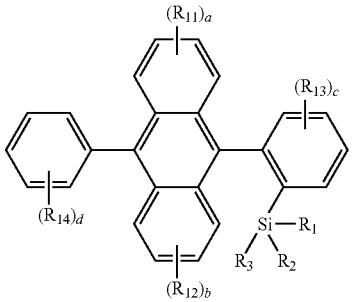

where $R_1$-$R_6$, $R_{11}$-$R_{14}$, and a-d are as defined in claim 1.

3. The cascade-type compound of claim 2, wherein the cascade-type compound is represented by Formula 1A or 1D, where $R_1$-$R_6$, $R_{11}$-$R_{14}$, and a-d are as defined in claim 1.

4. The cascade-type compound of claim 1, wherein $R_1$, $R_2$, $R_4$, and $R_5$ are each independently a substituted or unsubstituted $C_1$-$C_{20}$ alkyl group;

$R_3$ is a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted biphenylenyl group, a substituted or unsubstituted indacenyl group, a substituted or unsubstituted acenaphthylenyl group, a substituted or unsubstituted fluorenyl group, a substituted or unsubstituted spiro-fluorenyl group, a substituted or unsubstituted carbazolyl group, a substituted or unsubstituted anthryl group, a substituted or unsubstituted phenalenyl group, a substituted or unsubstituted phenanthrenyl group, a substituted or unsubstituted chrysenyl group, a substituted or unsubstituted triphenylenyl group, a substituted or unsubstituted pyrenyl group, a substituted or unsubstituted perylenyl group, a substituted or unsubstituted fluoranthenyl group, a substituted or unsubstituted naphthacenyl group, a substituted or unsubstituted picenyl group, a substituted or unsubstituted pentaphenyl group, a substituted or unsubstituted hexacenyl group, a substituted or unsubstituted dibenzofuranyl group, a substituted or unsubstituted dibenzothiophenyl group, a substituted or unsubstituted phenothiazinyl group, a substituted or unsubstituted phenoxazinyl group, a substituted or unsubstituted dihydrophenazinyl group, a substituted or unsubstituted phenoxathiinyl group, or a substituted or unsubstituted phenanthridinyl group; and $R_6$ is a substituted or unsubstituted cyclopropyl group, a substituted or unsubstituted cyclobutyl group, a substituted or unsubstituted cyclopentyl group, a substituted or unsubstituted cyclohexyl group, a substituted or unsubstituted cycloheptyl group, a substituted or unsubstituted cyclooctyl group, a substituted or unsubstituted cyclopentenyl group, a substituted or unsubstituted cyclopentadienyl group, a substituted or unsubstituted cyclohexcenyl group, a substituted or unsubstituted cyclohexadienyl group, a substituted or unsubstituted cycloheptadienyl group, a substituted or unsubstituted thiophenyl group, a substituted or unsubstituted furanyl group, a substituted or unsubstituted pyrrolyl group, a substituted or unsubstituted imidazolyl group, a substituted or unsubstituted pyrazolyl group, a substituted or unsubstituted isothiazolyl group, a substituted or unsubstituted isoxazolyl group, a substituted or unsubstituted thiazolyl group, a substituted or unsubstituted oxazolyl group, a substituted or unsubstituted oxadiazolyl group, a substituted or unsubstituted thiadiazolyl group, a substituted or unsubstituted triazolyl group, a substituted or unsubstituted phenyl group, a substituted or unsubstituted pyridinyl group, a substituted or unsubstituted pyrazinyl group, a substituted or unsubstituted pyrimidinyl group, a substituted or unsubstituted pyridazinyl group, or a substituted or unsubstituted triazinyl group.

5. The cascade-type compound of claim 1, wherein $R_1$, $R_2$, $R_4$, and $R_5$ are each independently one of a $C_1$-$C_{20}$ alkyl group; and a $C_1$-$C_{20}$ alkyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —$N(Q_{11})(Q_{12})$, wherein $Q_{11}$ and $Q_{12}$ are each independently a hydrogen atom, a $C_1$-$C_{10}$ alkyl group, a $C_6$-$C_{20}$ aryl group or a $C_2$-$C_{20}$ heteroaryl group;

$R_3$ is one of a pentalenyl group, an indenyl group, a naphthyl group, an azulenyl group, a heptalenyl group, a biphenylenyl group, an indacenyl group, an acenaphthylenyl group, a fluorenyl group, a spiro-fluorenyl group, a carbazolyl group, an anthryl group, a phenalenyl group, a phenanthrenyl group, a perylenyl group, a fluoranthenyl group, a naphthacenyl group, a picenyl group, pentaphenyl group, a hexacenyl group, a dibenzofuranyl group, a dibenzothiophenyl group, a phenothiazinyl group, a phenoxazinyl group, a dihydrophenazinyl group, a phenoxathiinyl group, and a phenanthridinyl group; and a pentalenyl group, an indenyl group, a naphthyl group, an azulenyl group, a heptalenyl group, a biphenylenyl group, an indacenyl group, an acenaphthylenyl group, a fluorenyl group, a spiro-fluorenyl group, a carbazolyl group, an anthryl group, a phenalenyl group, a phenanthrenyl group, a perylenyl group, a fluoranthenyl group, a naphthacenyl group, a picenyl group, a pentaphenyl group, a hexacenyl group, a dibenzofuranyl group, a dibenzothiophenyl group, a phenothiazinyl group, a phenoxazinyl group, a dihydrophenazinyl group, a phenoxathiinyl group, and a phenanthridinyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —$N(Q_{11})(Q_{12})$, wherein $Q_{11}$ and $Q_{12}$ are each independently a hydrogen atom, a $C_1$-$C_{10}$ alkyl group, a $C_6$-$C_{20}$ aryl group, or a $C_2$-$C_{20}$ heteroaryl group; and $R_6$ is one of a cyclopropyl group, a cyclobutyl group, a cyclopentyl group, a cyclohexyl group, a cycloheptyl group, a cyclooctyl group, a cyclopentenyl group, a cyclopentadienyl group, a cyclohexcenyl group, a cyclohexadienyl group, a cycloheptadienyl group, a thiophenyl group, a furanyl group, a pyrrolyl group, an imidazolyl group, a pyrazolyl group, an isothiazolyl group, an isoxazolyl group, a thiazolyl group, an oxazolyl group, an oxadiazolyl group, a thiadiazolyl group, a triazolyl group, a phenyl group, a pyridinyl group, a pyrazinyl group, a pyrimidinyl group, a pyridazinyl group, and a triazinyl group; and a cyclopropyl group, a cyclobutyl group, a cyclopentyl group, a cyclohexyl group, a cycloheptyl group, a cyclooctyl group, a cyclopentenyl group, a cyclopentadienyl group, a cyclohexcenyl group, a cyclohexadienyl group, a cycloheptadienyl group, a thiophenyl group, a furanyl group, a pyrrolyl group, an imidazolyl group, a pyrazolyl group, an isothiazolyl group, an isoxazolyl group, a thiazolyl group, an oxazolyl group, an oxadiazolyl group, a thiadiazolyl group, a triazolyl group, a phenyl group, a pyridinyl group, a pyrazinyl group, a pyrimidinyl group, a pyridazinyl group, and a triazinyl group, that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —$N(Q_{11})(Q_{12})$, wherein $Q_{11}$ and $Q_{12}$ are each independently a hydrogen atom, a $C_1$-$C_{10}$ alkyl group, a $C_6$-$C_{20}$ aryl group or a $C_2$-$C_{20}$ heteroaryl group.

6. The cascade-type compound of claim 1, wherein $R_1$, $R_2$, $R_4$, and $R_5$ are each independently one of a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group; and a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —N($Q_{11}$)($Q_{12}$), wherein $Q_{11}$ and $Q_{12}$ are each independently a hydrogen atom, a $C_1$-$C_{10}$ alkyl group, a $C_6$-$C_{20}$ aryl group, or a $C_2$-$C_{20}$ heteroaryl group;

$R_3$ is one of the groups represented by Formulae 3A to 3R; and $R_6$ is one of the groups represented by Formulae 2A to 2T:

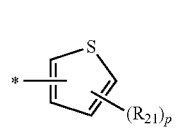

Formula 2A

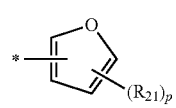

Formula 2B

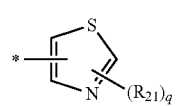

Formula 2C

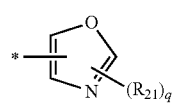

Formula 2D

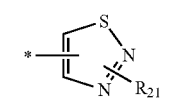

Formula 2E

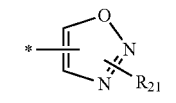

Formula 2F

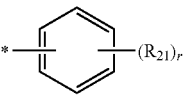

Formula 2G

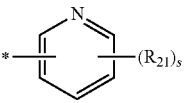

Formula 2H

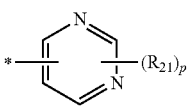

Formula 2I

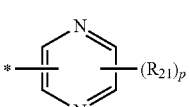

Formula 2J

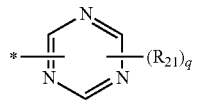

Formula 2K

Formula 2L

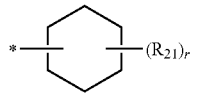

Formula 2M

Formula 2N

Formula 2O

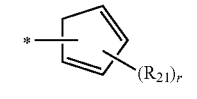

Formula 2P

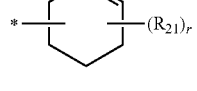

Formula 2Q

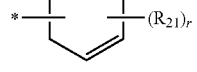

Formula 2R

Formula 2S

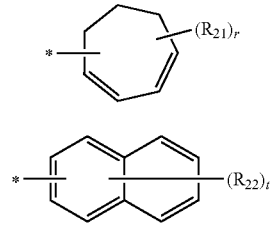

Formula 2T

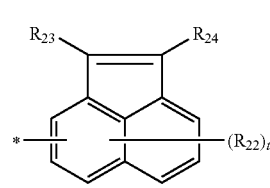

Formula 3A

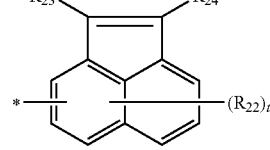

Formula 3B

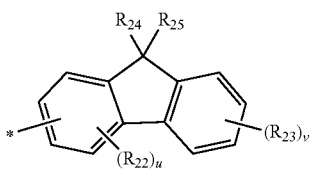

Formula 3C

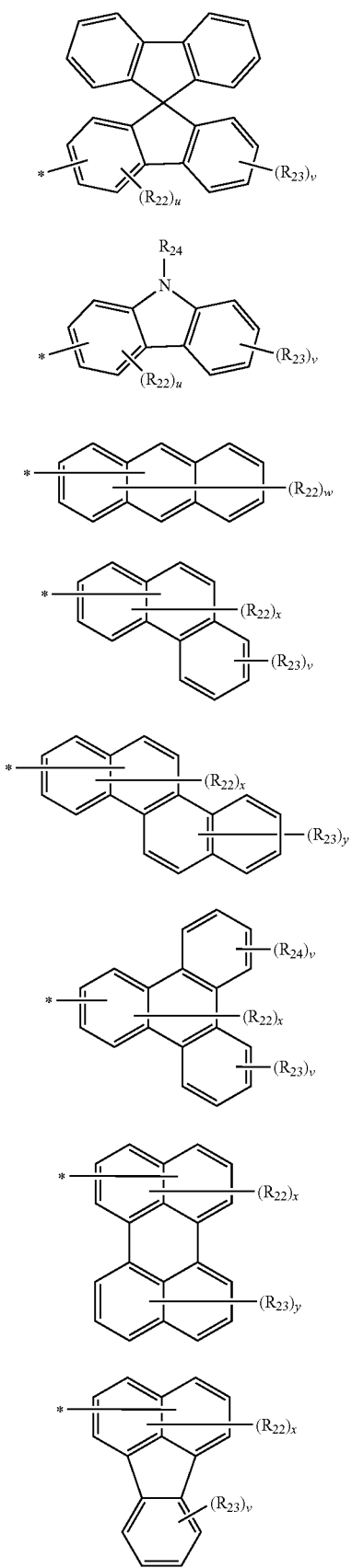

Formula 3D

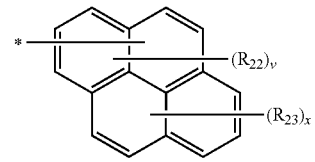

Formula 3L

Formula 3E

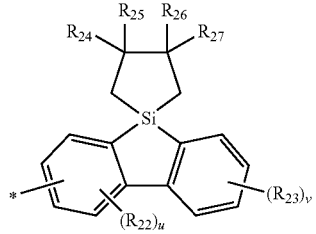

Formula 3M

Formula 3F

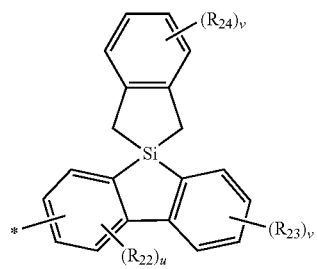

Formula 3N

Formula 3G

Formula 3H

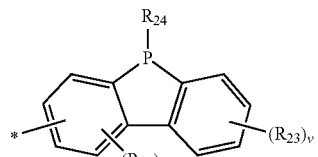

Formula 3O

Formula 3I

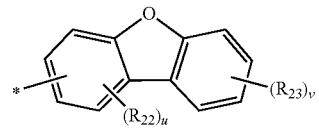

Formula 3P

Formula 3J

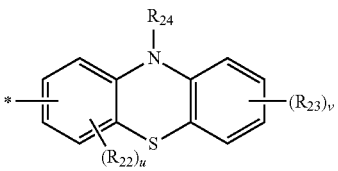

Formula 3Q

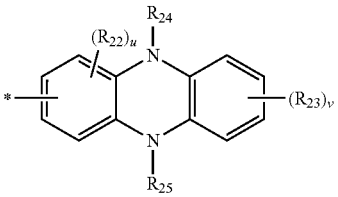

Formula 3R

Formula 3K wherein, in Formulae 2A to 2T and Formulae 3A to 3R:
$R_{21}$ to $R_{27}$ are each independently a hydrogen atom, a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, or —N($Q_{21}$)($Q_{22}$), wherein $Q_{21}$ and $Q_{22}$ are each independently a hydrogen atom, a $C_1$-$C_{10}$ alkyl group, a $C_6$-$C_{20}$ aryl group, or a $C_2$-$C_{20}$ heteroaryl group;

p and u are each independently an integer from 1 to 3;

q is 1 or 2;

r and x are each independently an integer from 1 to 5;

s and v are each independently an integer from 1 to 4;

t is an integer from 1 to 7;

w is an integer from 1 to 9; and y is an integer from 1 to 6.

7. The cascade-type compound of claim 1, wherein $R_1$, $R_2$, $R_4$, and $R_5$ are each independently one of a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group; and a methyl group, an ethyl group, an n-propyl group, an i-propyl group, an n-butyl group, an i-butyl group, a t-butyl group, a pentyl group, a hexyl group, a heptyl group, an octyl group, a nonyl group, and a decyl group that are substituted with at least one of a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a phenyl group, a naphthyl group, and an anthryl group;

$R_3$ is one of the groups represented by Formulae 4A to 4J; and $R_6$ is one of the groups represented by Formula 2G Formula 2G Formula 4A Formula 4B Formula 4C Formula 4D Formula 4E Formula 4F Formula 4G Formula 4H Formula 4I Formula 4J wherein, in Formula 2G and Formulae 4A to 4J:

$R_{21}$ to $R_{25}$ are each independently a hydrogen atom, a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a dimethyl-fluorenyl group, a phenyl-carbazolyl group, a pyrenyl group, a crysenyl group, a benzothiazolyl group, a benzoxazolyl group, a phenyl-benzoimidazolyl group, or —N($Q_{21}$)($Q_{22}$), wherein $Q_{21}$ and $Q_{22}$ are each independently a hydrogen atom, a $C_1$-$C_{10}$ alkyl group, a phenyl group, a naphthyl group, or an anthryl group;

r and x are each independently an integer from 1 to 5;

v is an integer from 1 to 4;

t is an integer from 1 to 7;
w is an integer from 1 to 9; and
y is an integer from 1 to 6.

8. The cascade-type compound of claim 1, wherein $R_1$, $R_2$, $R_4$, and $R_5$ are identical to each other, and $R_3$ and $R_6$ are identical to each other.

9. The cascade-type compound of claim 1, wherein $R_{11}$ to $R_{14}$ are each independently a hydrogen atom, a deuterium atom, a halogen atom, a hydroxyl group, a cyano group, a nitro group, an amino group, an amidino group, hydrazine, hydrazone, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a dimethylfluorenyl group, a phenyl-carbazolyl group, a pyrenyl group, or a crysenyl group.

10. The cascade-type compound of claim 1, wherein the cascade-type compound is one of Compounds 1 to 22 below:

1

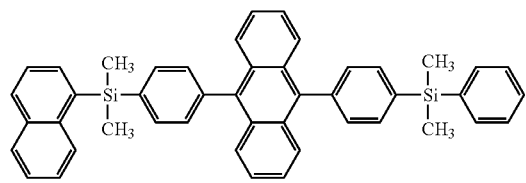

2

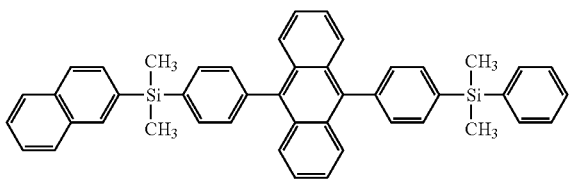

3

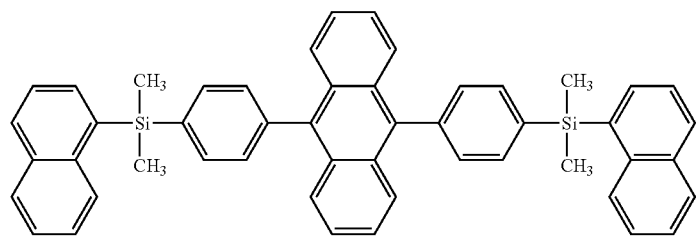

4

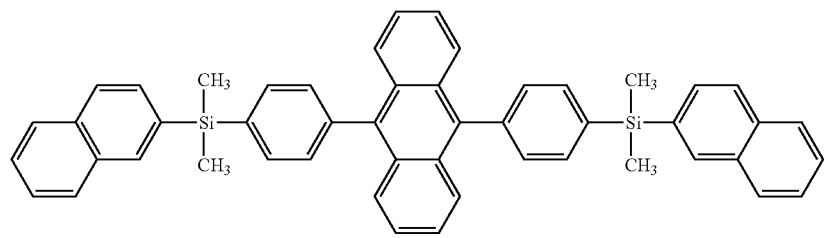

5

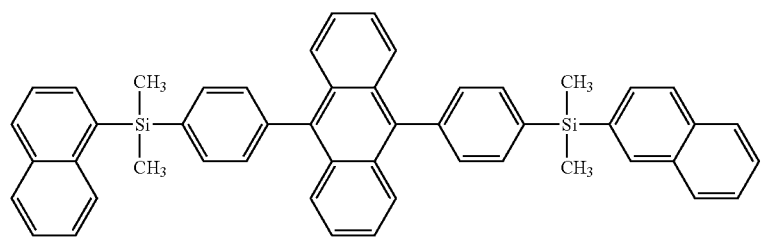

6

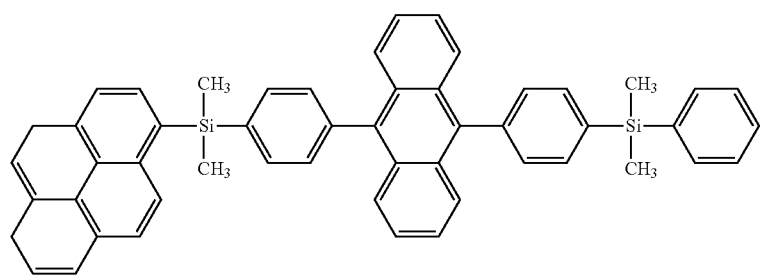

-continued
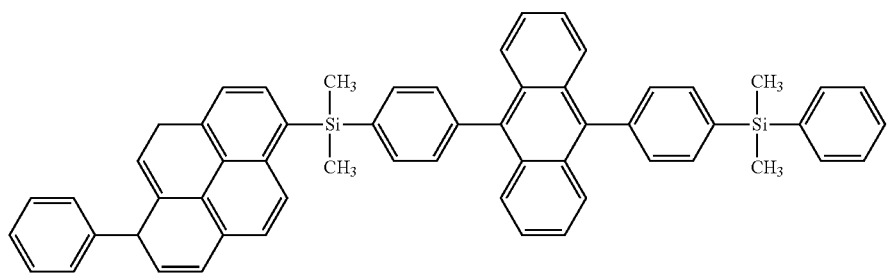
7
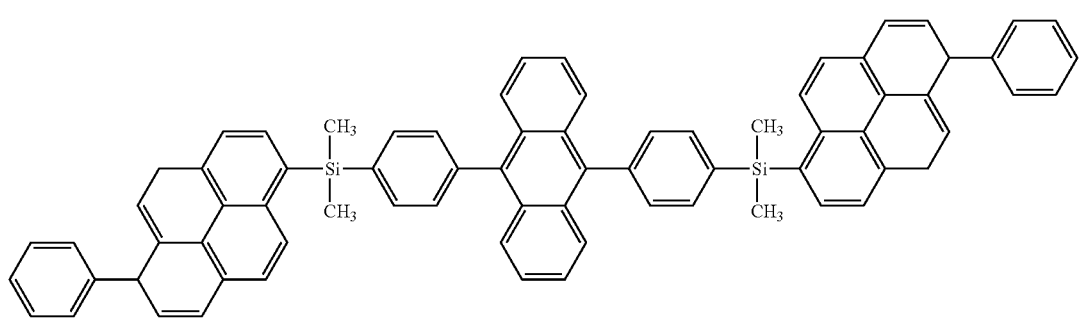
8
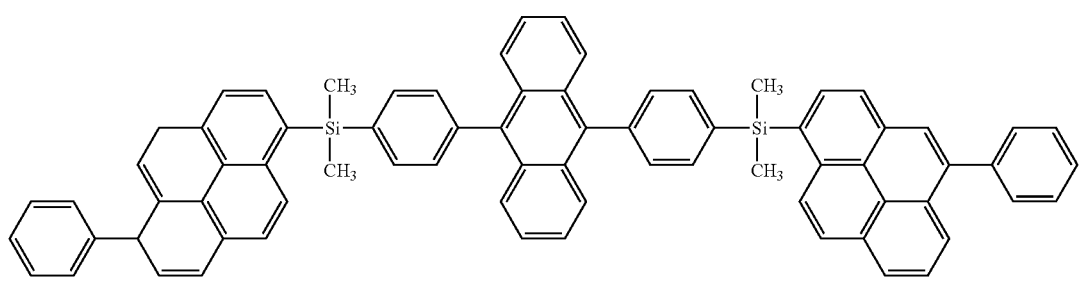
9
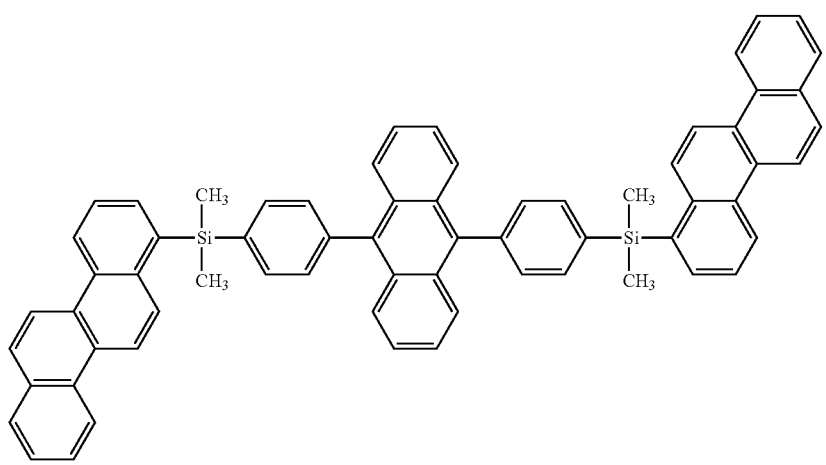
10

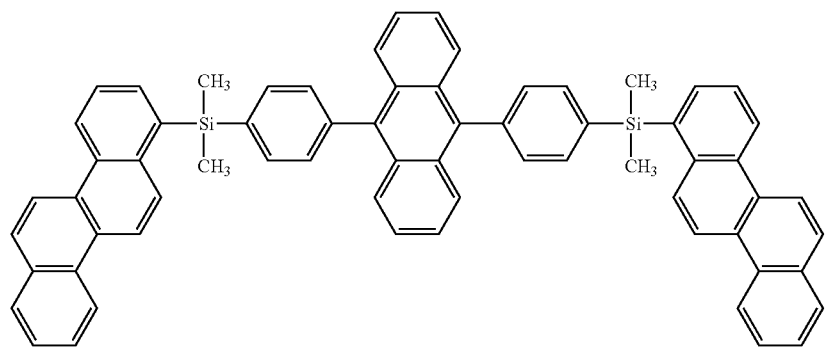
11
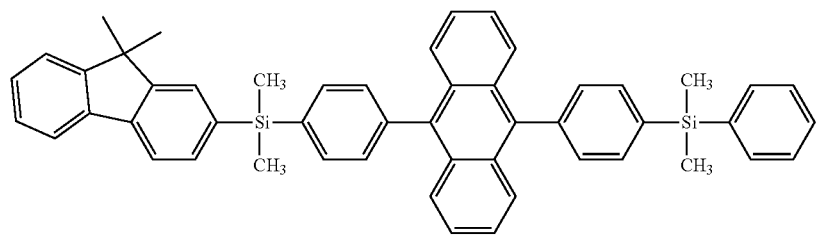
12
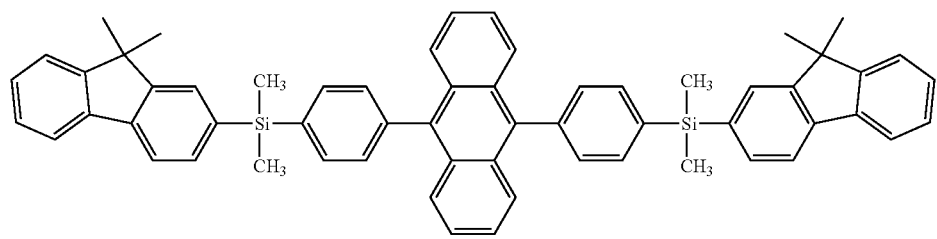
13
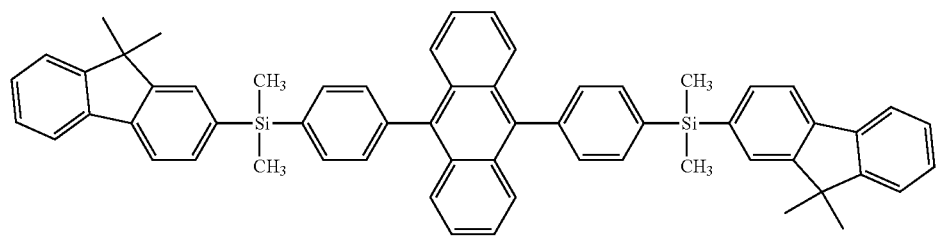
14
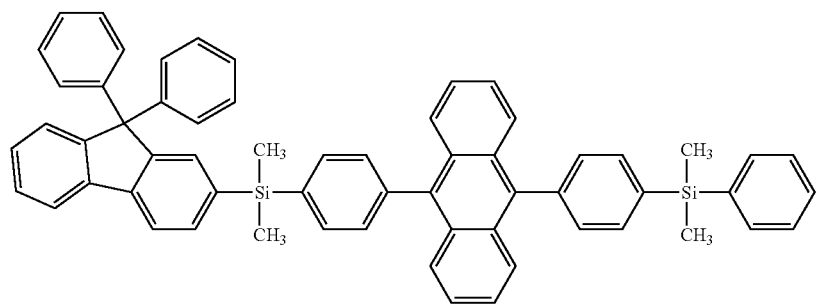
15

16
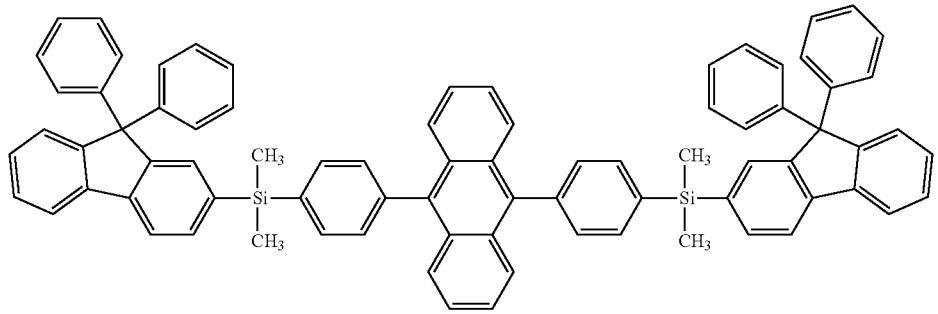
17
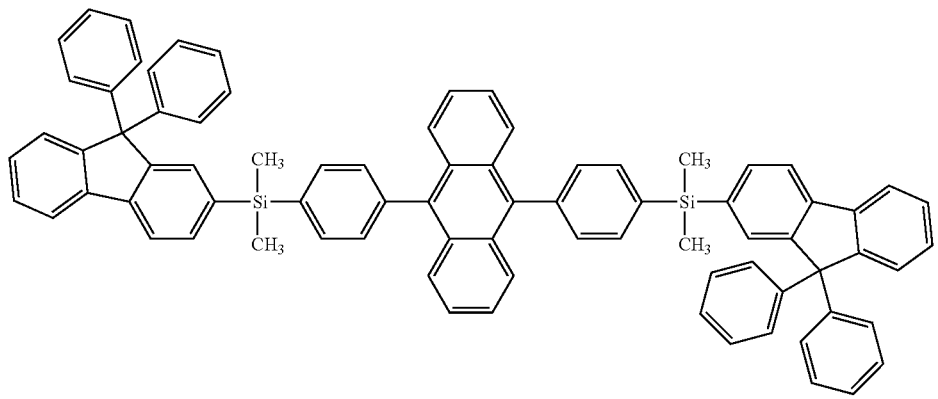
18
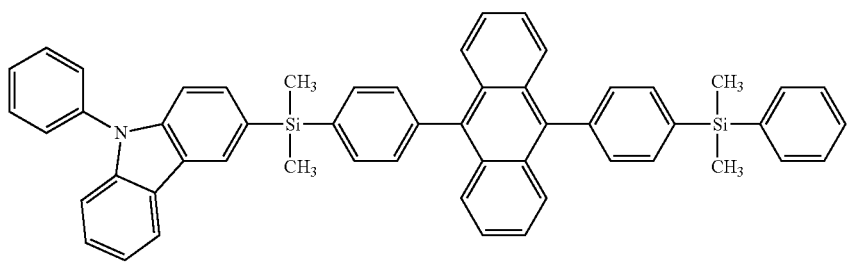
19
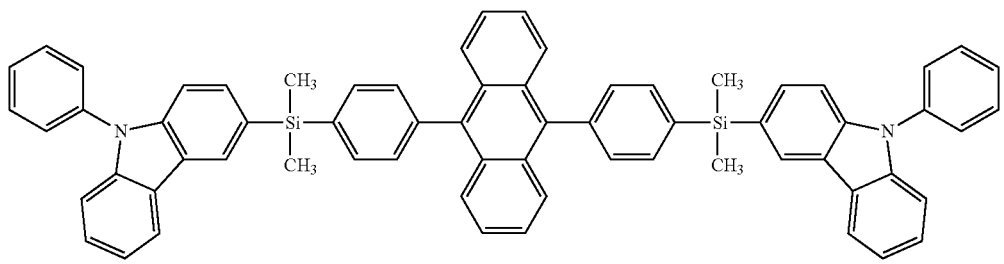
20
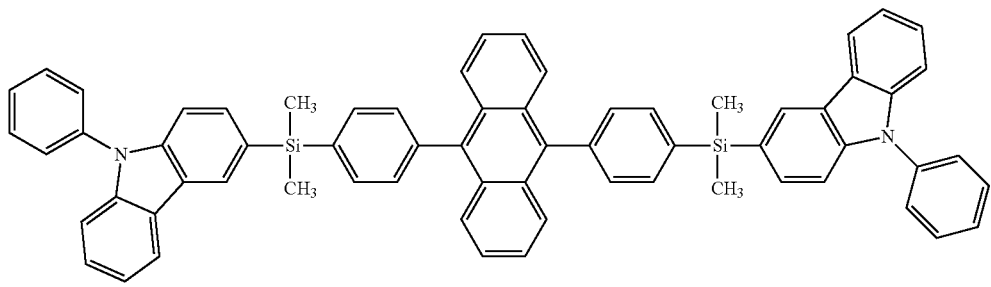

21

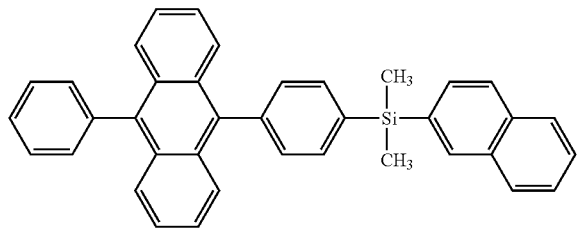

22

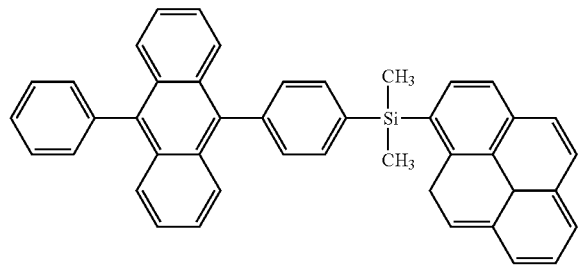

11. An organic light-emitting device, comprising:
a first electrode;
a second electrode disposed opposite to the first electrode; and
an organic layer disposed between the first electrode and the second electrode, the organic layer comprising at least one of a cascade-type compound of claim 1.

12. The organic light-emitting device of claim 11, wherein the organic layer comprises at least one of a hole injection layer, a hole transport layer, a functional layer having both hole injection and hole transport capabilities, a buffer layer, an electron blocking layer, an emission layer, a hole blocking layer, an electron transport layer, an electron injection layer, and a functional layer having both electron injection and electron transport capabilities.

13. The organic light-emitting device of claim 12, wherein the organic layer comprises an emission layer, and the cascade-type compound is included in the emission layer.

14. The organic light-emitting device of claim 12, wherein the organic layer comprises at least one of a hole injection layer, a hole transport layer, and a functional layer having both hole injection and hole transport capabilities, and the at least one of the hole injection layer, the hole transport layer, and the functional layer having both hole injection and hole transport capabilities comprises a charge-generating material.

15. The organic light-emitting device of claim 12, wherein the organic layer comprises an electron transport layer, and the electron transport layer comprises a metal-containing material.

* * * * *